(12) United States Patent
Locke et al.

(10) Patent No.: US 11,925,746 B2
(45) Date of Patent: Mar. 12, 2024

(54) NEGATIVE PRESSURE WOUND THERAPY SYSTEM WITH DYNAMIC FLUID DELIVERY

(71) Applicant: KCI Licensing, Inc., San Antonio, TX (US)

(72) Inventors: Christopher Brian Locke, Bournemouth (GB); Benjamin Andrew Pratt, Poole (GB)

(73) Assignee: 3M Innovative Properties Company, Saint Paul, MN (US)

( * ) Notice: Subject to any disclaimer, the term of this patent is extended or adjusted under 35 U.S.C. 154(b) by 124 days.

(21) Appl. No.: 17/602,541

(22) PCT Filed: May 5, 2020

(86) PCT No.: PCT/US2020/031418
§ 371 (c)(1),
(2) Date: Oct. 8, 2021

(87) PCT Pub. No.: WO2020/227258
PCT Pub. Date: Nov. 12, 2020

(65) Prior Publication Data
US 2022/0168494 A1 Jun. 2, 2022

Related U.S. Application Data

(60) Provisional application No. 62/844,291, filed on May 7, 2019.

(51) Int. Cl.
*A61M 1/00* (2006.01)
(52) U.S. Cl.
CPC ............. *A61M 1/912* (2021.05); *A61M 1/92* (2021.05); *A61M 1/96* (2021.05); *A61M 1/985* (2021.05);
(Continued)

(58) Field of Classification Search
CPC .......... A61M 1/90; A61M 1/912; A61M 1/92; A61M 1/985; A61M 1/96; A61M 2205/3334; A61M 2205/3379
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Susan S Su
*Assistant Examiner* — Ted Yang

(57) ABSTRACT

One implementation of the present disclosure is a negative pressure wound therapy (NPWT) system, according to some embodiments. In some embodiments, the system includes an instillation system configured to provide instillation fluid to a wound site, and a controller. In some embodiments, the wound site includes a wound and a wound dressing. In some embodiments, the controller is configured to provide a first quantity of instillation fluid for a first instillation cycle. In some embodiments, the controller is configured to determine a second quantity of instillation fluid for a second instillation cycle based on the first quantity and a reduction factor. In some embodiments, the second quantity of instillation fluid is less than the first quantity of instillation fluid. In some
(Continued)

embodiments, the controller is configured to adjust an operation of the instillation system to provide the second quantity of instillation fluid to the wound site.

13 Claims, 11 Drawing Sheets

(52) U.S. Cl.
CPC ............... *A61M 2205/3334* (2013.01); *A61M 2205/3379* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2013/0211318 A1* | 8/2013 | Croizat | A61M 3/0208 604/23 |
| 2014/0163491 A1 | 6/2014 | Schuessler et al. | |
| 2015/0080788 A1 | 3/2015 | Blott et al. | |
| 2017/0182230 A1* | 6/2017 | Ingram | A21B 3/18 |
| 2018/0214315 A1* | 8/2018 | Mercer | A61M 39/08 |
| 2019/0365961 A1* | 12/2019 | Walti | A61M 1/98 |
| 2020/0038249 A1* | 2/2020 | Pratt | A61M 1/95 |
| 2020/0139024 A1* | 5/2020 | Pratt | A61M 1/85 |
| 2020/0229983 A1* | 7/2020 | Robinson | A61F 13/00068 |
| 2020/0246194 A1* | 8/2020 | Gonzalez | A61B 5/445 |
| 2020/0306426 A1* | 10/2020 | Rice | A61M 1/772 |
| 2021/0045927 A1* | 2/2021 | Locke | A61M 1/915 |
| 2021/0077302 A1* | 3/2021 | Carroll | A61L 15/425 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3740179 B1 * 3/2022 ....... A61F 13/00055 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| KR | 101685509 B1 | 12/2016 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | WO-2015094724 A1 * 6/2015 ....... A61F 13/00068 |
| WO | WO-2019136164 A1 * 7/2019 ....... A61F 13/00017 |
| WO | WO-2020197551 A1 * 10/2020 ............ A61B 5/445 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

International Search Report and Written Opinion for Corresponding Application No. PCT/US2020/031418 dated Sep. 4, 2020.

Chinese Office Action for corresponding application 202080031653X, dated Jun. 30, 2023.

\* cited by examiner

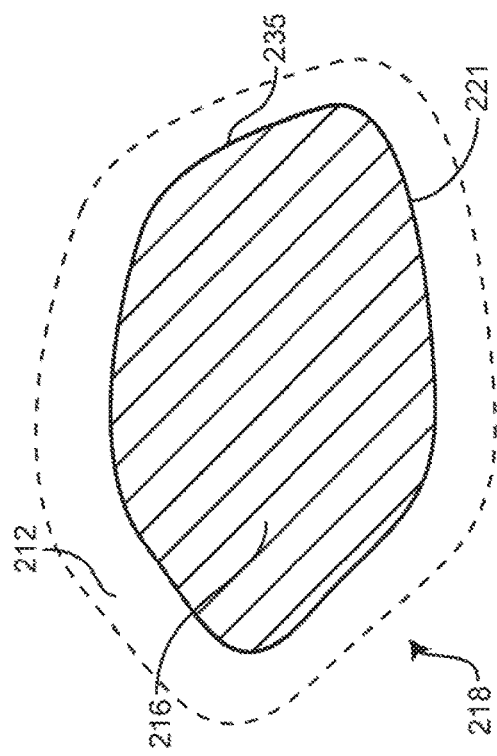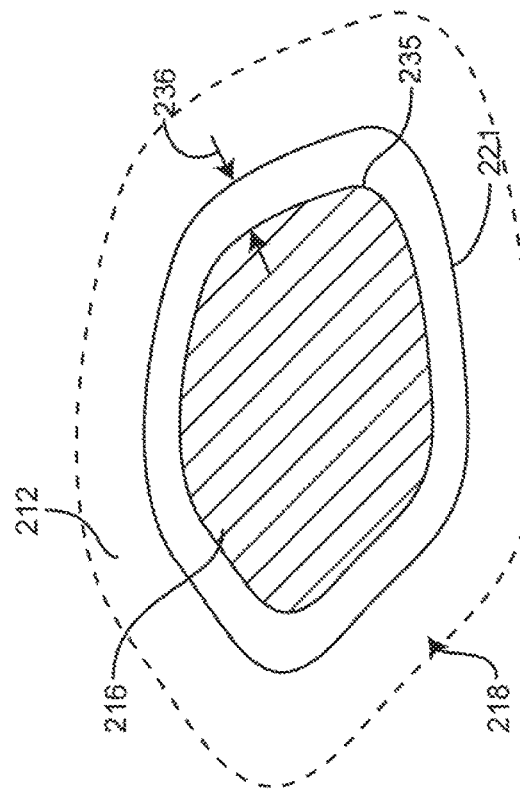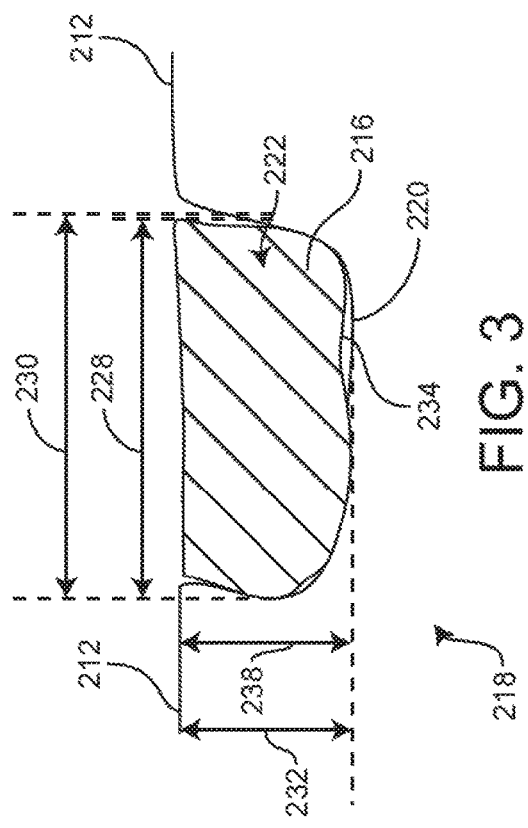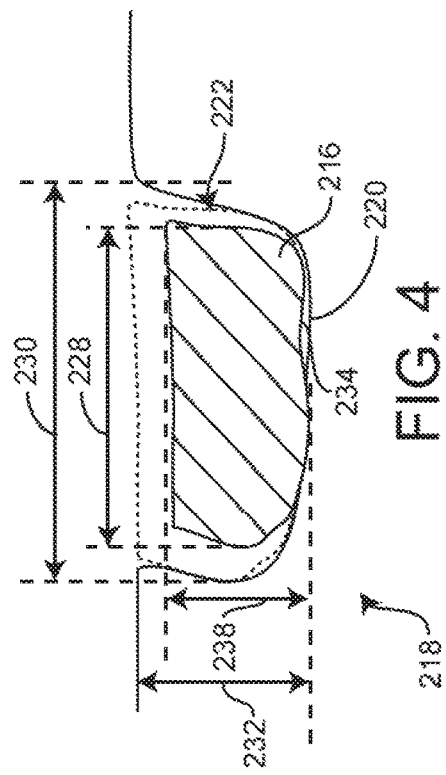

NEGATIVE PRESSURE WOUND THERAPY SYSTEM WITH DYNAMIC FLUID DELIVERY

CROSS-REFERENCE TO RELATED APPLICATIONS

This application claims the benefit of priority to U.S. Provisional Application No. 62/844,291, filed on May 7, 2019, which is incorporated herein by reference in its entirety.

BACKGROUND

The present disclosure relates generally to negative pressure wound therapy (NPWT) devices and more particularly control algorithms for NPWT devices. Some NPWT devices introduce a cleansing fluid to a wound before a negative pressure is drawn at the wound. Unfortunately, many systems provide an excessive amount of instillation fluid to the wound, or do not account for changes in fluid capacity of the wound over time. This results in frequent leakages and reduction of NPWT quality. There is a need for a NPWT device which takes into account therapy duration and does not overfill the wound with instillation fluid.

SUMMARY

One implementation of the present disclosure is a negative pressure wound therapy (NPWT) system, according to some embodiments. In some embodiments, the system includes an installation system configured to provide instillation fluid to a wound site, and a controller. In some embodiments, the wound site includes a wound and a wound dressing. In some embodiments, the controller is configured to provide a first quantity of instillation fluid for a first installation cycle. In some embodiments, the controller is configured to determine a second quantity of instillation fluid for a second installation cycle based on the first quantity and a reduction factor. In some embodiments, the second quantity of instillation fluid is less than the first quantity of instillation fluid. In some embodiments, the controller is configured to adjust an operation of the instillation system to provide the second quantity of instillation fluid to the wound site.

In some embodiments, the reduction factor is determined based on a negative pressure of a negative pressure cycle and a time duration of the negative pressure cycle.

In some embodiments, the reduction factor is determined based on an amount of compression of the wound dressing over a time period.

In some embodiments, the wound dressing includes one or more foam pieces.

In some embodiments, the controller is configured to receive an initial volume value of the wound from a user interface and use the initial volume value of the wound to determine the first quantity of instillation fluid.

In some embodiments, the controller is configured to determine the second quantity of instillation fluid for the second instillation cycle by determining a decrease amount based on the reduction factor and the first quantity.

In some embodiments, the second quantity is a difference between the first quantity and the first quantity multiplied by the reduction factor.

In some embodiments, the reduction factor is a normalized value.

In some embodiments, the controller is configured to select the reduction factor from a database of reduction factors based on a negative pressure of a negative pressure cycle and a duration of the negative pressure cycle.

Another implementation of the present disclosure is a NPWT device configured to provide fluid to a wound and produce a negative pressure at the wound for NPWT, according to some embodiments. In some embodiments, the NPWT device includes a controller configured to monitor the negative pressure at the wound and an elapsed amount of therapy time, select a reduction factor based on the monitored negative pressure at the wound and the monitored amount of therapy time, determine a reduced value of fluid volume to provide to the wound based on a previous value of fluid volume provided to the wound and the reduction factor, and cause the NPWT device to provide the reduced value of fluid volume to the wound. In some embodiments, the reduced value of fluid volume is less than the previous value of fluid volume provided to the wound.

In some embodiments, the reduction factor is a percentage value.

In some embodiments, the reduced value of fluid volume is determined by decreasing the previous value of fluid volume by the percentage value.

In some embodiments, the percentage value selected by the controller is between three and six percent if the monitored negative pressure at the wound is between 70 and 80 mmHg and the elapsed amount of therapy time is a predetermined time quantity.

In some embodiments, the percentage value selected by the controller is between seven and nine percent if the monitored negative pressure at the wound is between 145 and 155 mmHg and the elapsed amount of therapy time is a predetermined time quantity.

In some embodiments, the percentage value selected by the controller is between nine and eleven percent if the monitored negative pressure at the wound is between 195 and 205 mmHg and the elapsed amount of therapy time is a predetermined time quantity.

In some embodiments, the reduction factor is determined based on an empirical relationship between an amount of therapy time at a negative pressure value and an amount of compression of a wound dressing.

Another implementation of the present disclosure relates to a method for adjusting and providing a quantity of instillation fluid to a wound site, according to some embodiments. In some embodiments, the method includes monitoring an amount of elapsed time of negative pressure wound therapy (NPWT), determining a reduction amount based on a negative pressure setpoint of the NPWT during the elapsed time, and the amount of elapsed time of NPWT, determining a reduced instillation fluid quantity by reducing a previously provided instillation quantity by the reduction amount, and providing the reduced instillation quantity of instillation fluid to the wound site via an instillation system.

In some embodiments, the reduction amount is determined based on a reduction percentage and the previously provided instillation quantity.

In some embodiments, the reduction percentage is determined based on the amount of elapsed time and the negative pressure setpoint of the NPWT during the elapsed time.

In some embodiments, the reduction percentage is selected from a set of reduction percentages based on the amount of elapsed time and the negative pressure setpoint of the NPWT during the elapsed time.

BRIEF DESCRIPTION OF THE DRAWINGS

FIG. 3 is a side view of the dressing and the wound of the wound site of FIG. 2, according to some embodiments.

FIG. 4 is a side view of the dressing and the wound of the wound site of FIG. 2, after the dressing has compressed an amount, according to some embodiments.

FIG. 5 is a top view of the dressing and the wound of the wound site of FIG. 2, according to some embodiments.

FIG. 6 is a top view of the dressing and the wound of the wound site of FIG. 2, after the dressing has compressed an amount, according to some embodiments.

DETAILED DESCRIPTION

Overview

Referring generally to the FIGURES, systems, methods, and devices for dynamically adjusting an amount of instillation fluid provided to a wound is shown, according to some embodiments. Often times, wound volume may change due to compression set of dressings/foam, swelling of tissue, granulation tissue formation, and healing of the wound. This may result in a reduced amount of required instillation fluid (e.g., Saline) as the NPWT is performed. Users may often over-fill a fluid instillation reservoir, thereby providing an excessive amount of fluid to the wound. This may cause leakages, which can adversely affect the healing process, and can cause messes if the instillation fluid leaks onto a user. Due to these factors, the amount of instillation fluid required decreases as NPWT is performed. A controller receives various user and sensor inputs regarding a type of NPWT being performed, a duration of NPWT, a vacuum pressure of the NPWT, etc. The controller can determine or select a reduction factor based on the vacuum pressure of the NPWT and the duration of the NPWT. The controller can determine a reduced instillation volume for a future fluid instillation cycle based on the reduction factor and a previously provided volume of instillation fluid. Advantageously, the controller can adjust the amount or volume of instillation fluid provided to the wound over time to reduce the likelihood of leakages. The reduction factor can take into account soak time. The reduction factor can be selected from a table, or determined using a function derived from an empirical relationship.

NPWT Device

Figure 1:
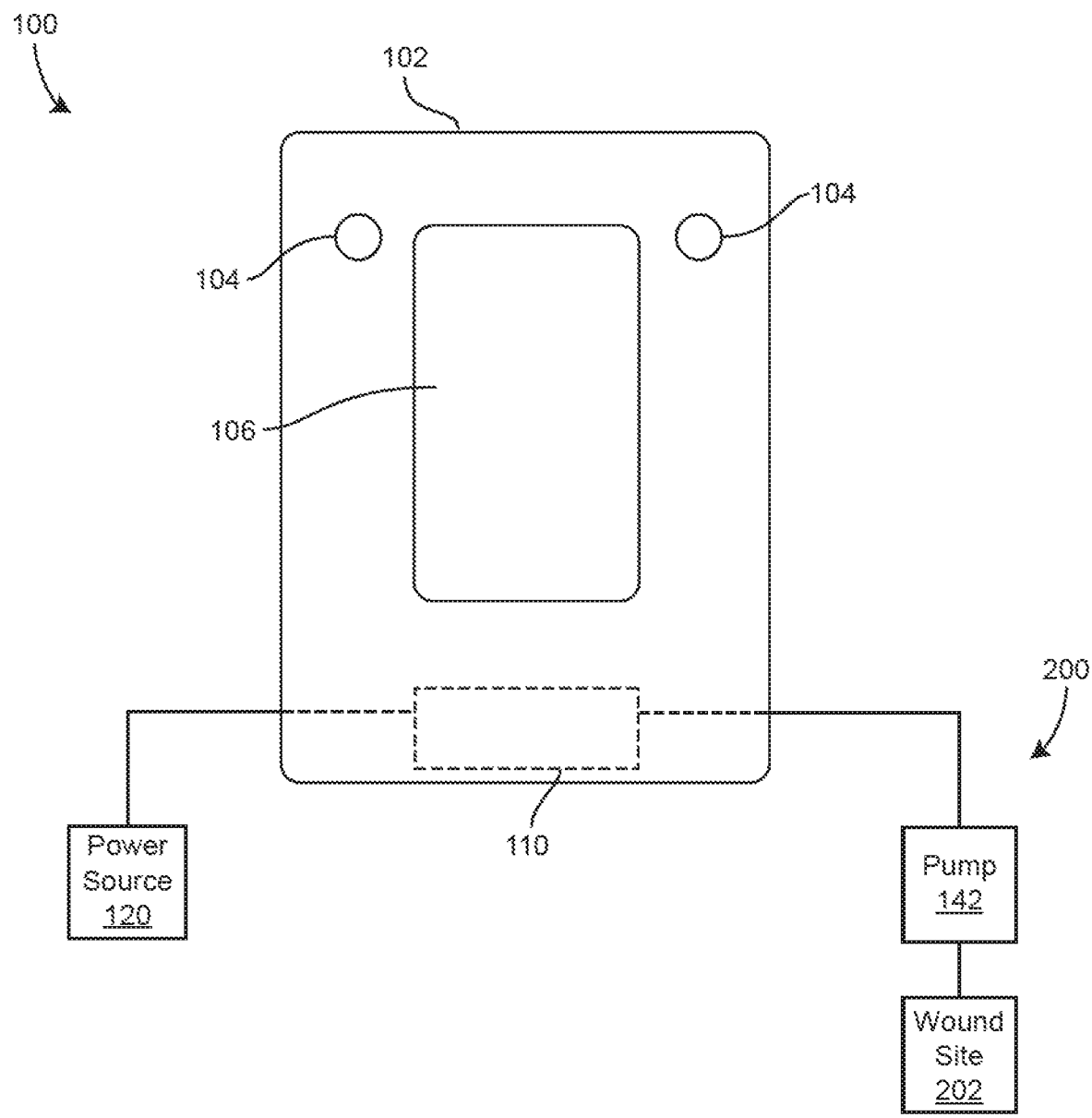
FIG. 1 is a block diagram of a NPWT device for a NPWT application system including a user interface, a controller, and a pump, according to some embodiments.

Referring now to FIG. 1, a front view of a NPWT device 100 is shown, according to an exemplary embodiment. The NPWT device 100 includes a user interface 106, buttons 104, a housing 102, and a controller 110, according to some embodiments. In some embodiments, controller 110 is configured control a NPWT application system 200 to perform NPWT for a wound side 202. In some embodiments, controller 110 is configured to control an operation of pump 142 to perform NPWT for wound side 202. NPWT application system 200 may include pump 142, instillation fluid reservoir 204, removed fluid reservoir 206, and pipes 208 and 210 (see FIG. 2), according to some embodiments. In some embodiments, NPWT device 100 is configured to control an operation of a V.A.C. VERAFLO™ Therapy, a PREVENA™ Therapy, an ABTHERA™ Open Abdomen Negative Pressure Therapy, or any other NPWT (e.g., controller 110 is configured to adjust an operation of pump 142 and/or NPWT application system 200 to perform any of the herein mentioned NPWT). In some embodiments, NPWT device 100 is configured to control an operation of any devices necessary to complete any of the herein mentioned NPWT (e.g., a pump, a vacuum system, an instillation system, etc.). In some embodiments, NPWT device 100 is a disposable NPWT device (dNPWT) and may have reusable/disposable parts. For example, NPWT device 100 may be relatively lightweight (e.g., less than 5 pounds), and may be portable, allowing a patient to transport NPWT device 100 while NPWT device 100 still performs NPWT, according to some embodiments. Since NPWT device 100 may be portable, NPWT device 100 may draw power from a portable power source (e.g., power source 120, a battery, etc.). The portable power source may have a limited energy capacity. Additionally, power source 120 may be a MAINS power source (e.g., a wall outlet).

User interface 106 is configured to display any of an alarm/alert regarding at least one of a battery capacity of NPWT device 100, a leak, a pump duty cycle/pump duty value, etc., according to some embodiments. In some embodiments, user interface 106 is configured to provide any of a visual and an auditory alert. In some embodiments, user interface 106 allows a user to adjust an operation of the NPWT performed by NPWT device 100. For example, the user may provide a user input to controller 110 through user interface 106 to increase a therapy pressure setpoint $p_{sp}$ of pump 142, adjust a type of NPWT performed, adjust a parameter/operation of the performed NPWT, adjust a duration of the performed NPWT, pause the NPWT, start the NPWT, transition the NPWT device 100 into a "change" mode (e.g., so that wound dressings can be changed), etc. In some embodiments user interface 106 displays an amount of instillation fluid for a user to provide. In some embodiments, user interface 106 receives an input of wound volume from a user. In some embodiments, user interface 106 is any of a resistive touch-screen interface, a surface acoustic wave touch-screen interface, a capacitive touch-screen interface, etc., configured to allow the user to control NPWT device 100. In some embodiments, user interface 106 is controlled by buttons 104. In some embodiments, buttons 104 are configured to control user interface 106 and/or to adjust an operation of the NPWT performed by NPWT device 100.

Figure 2:
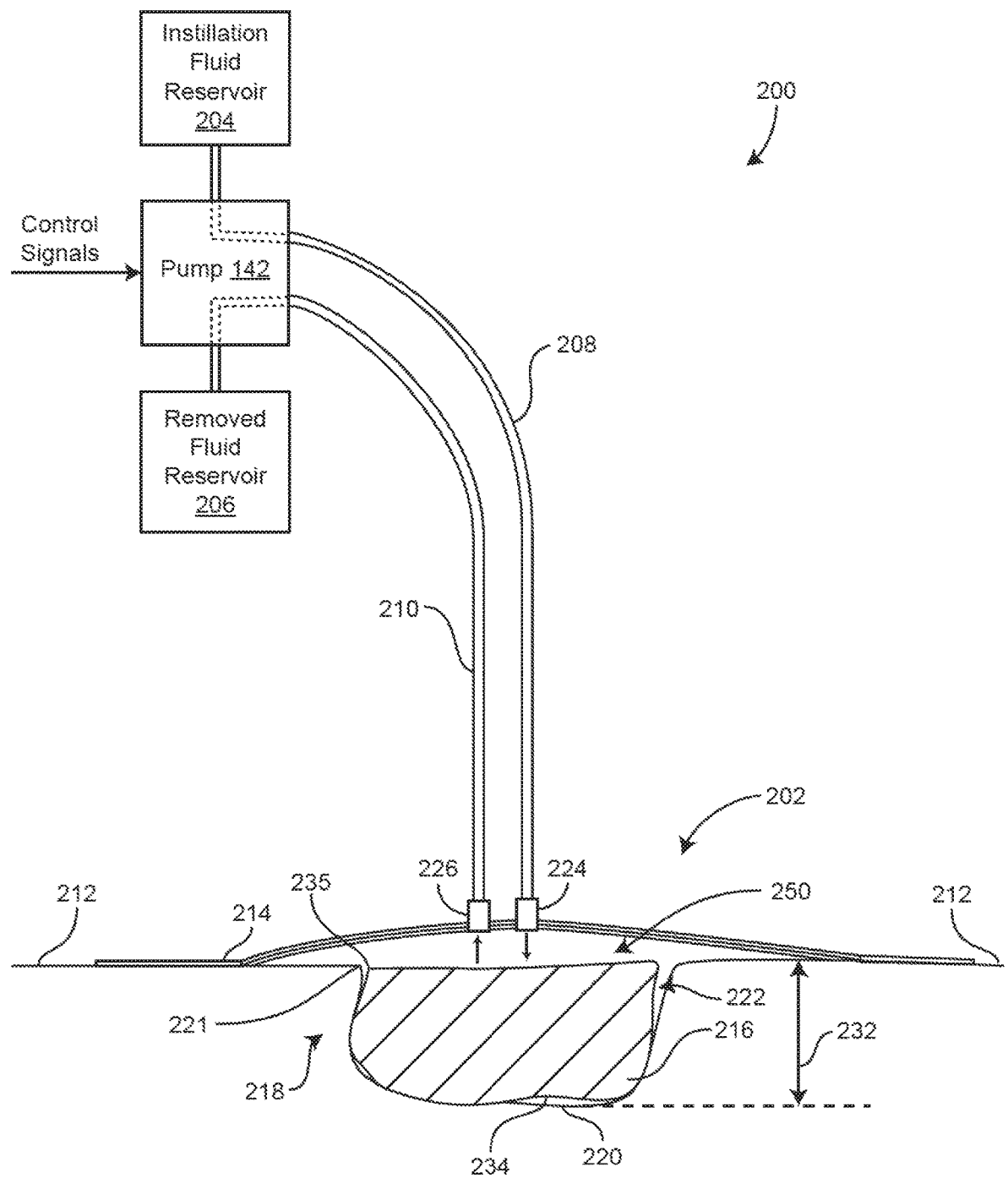
FIG. 2 is a block diagram of the NPWT application system of FIG. 1 including tubing configured to provide instillation fluid to a wound and a dressing of a wound site and generate a negative pressure at the wound site, according to some embodiments.

User interface 106 is also configured to display an operational status of the performed NPWT, according to some embodiments. For example, user interface 106 may display any of a patient name, a responsible caregiver's name, a type of NPWT currently being performed by NPWT device 100, a duration of NPWT, a time remaining in the current NPWT, a vacuum pressure of the NPWT, etc., or any other information relevant to the NPWT and/or operational status of NPWT device 100. For example, user interface 106 is configured to display a remaining battery life of a battery (e.g., power source 120 as shown in FIG. 2), and/or a duty cycle of the system configured to provide vacuum pressure to a wound (e.g., pump 142), according to some embodiments. In some embodiments, the remaining battery life of the battery is a remaining amount of energy in the battery. In some embodiments, the remaining battery life of the battery is a remaining amount of time which NPWT device 100 can sustain NPWT device at a current operational status. In some embodiments, user interface 106 is configured to communicably connect with controller 110. In some embodiments, user interface 106 provides controller 110 with any user inputs (e.g., therapy pressure setpoints, type of therapy selected, etc.). In some embodiments, controller 110 causes user interface 106 to display operational parameters of the NPWT, alarms, alerts, requests, etc.

In some embodiments, user interface 106 is a touchscreen. For example, user interface 106 may be any of a capacitive touch screen, a resistive touch screen, etc. In some embodiments, user interface 106 is configured to receive user inputs via the touchscreen and provide the user inputs to controller 110.

NPWT Application System

Referring now to FIG. 2, NPWT application system 200 is shown in greater detail, according to some embodiments. NPWT application system 200 includes pump 142, instillation fluid reservoir 204, removed fluid reservoir 206, return tubing 210, and supply tubing 208, according to some embodiments. In some embodiments, pump 142 is configured to draw a negative pressure at a wound site 202 via return tubing 210. In some embodiments, pump 142 draws the negative pressure at wound site 202 at the therapy pressure setpoint $p_{sp}$. In some embodiments, NPWT application system 200 is configured to provide an amount of instillation fluid (e.g., a Saline solution, etc.) to wound site 202 or to an inner volume 222 of wound 218 via supply tube 208. In some embodiments, NPWT application system 200 provides the instillation fluid to the wound side 202 and/or to inner volume 222 of the wound 218 from instillation fluid reservoir 204 via supply tube 208. In some embodiments, the instillation fluid is a sterile fluid which can be used for wounds which require washing to prevent infection or to reduce an amount of infection of the wound.

Supply tube 208 and return tube 210 may be any form of piping, medical tubing, flexible tubing, etc., having an inner volume configured to facilitate a flow of fluid, gas, solution, etc., therewithin and having sufficient structural strength to maintain a negative pressure (e.g., sufficient strength to not collapse while a negative pressure is produced within the inner volume). In some embodiments, supply tube 208 and return tube 210 are connected at a first end to pump 142, and/or instillation fluid reservoir 204, and/or removed fluid reservoir 206. For example, supply tube 208 may be fluidly connected with instillation fluid reservoir 204 to provide fresh instillation fluid to wound site 202. Likewise, return tube 210 may be fluidly connected to removed fluid reservoir 206 to remove fluid from wound site 202. In some embodiments, NPWT application system 200 may supply fresh instillation fluid to wound site 202 via pump 142. In some embodiments, pump 142 includes one or more pumps. For example, a separate pump may be provided to supply a positive pressure to push instillation fluid into wound site 202 via supply tube 208. In some embodiments, pump 142 provides a negative pressure to wound site 202 via return tubing 210. In some embodiments, the negative pressure provided via return tubing 210 provides a negative pressure at inner volume 250. In some embodiments, the negative pressure of inner volume 250 produced by pump 142 draws instillation fluid from instillation fluid reservoir 204. In some embodiments, a fluid regulatory device is positioned in line with supply tubing 208 to ensure that a sufficient volume or a sufficient volumetric flow rate of instillation fluid is provided to wound site 202 via supply tubing 208. In some embodiments, NPWT application system 200 actuates between NPWT cycles and fluid instillation cycles. For example, pump 142 is shown receiving control signals (e.g., from controller 110), according to some embodiments. In some embodiments, pump 142 initiates a fluid instillation cycle where instillation fluid is provided to wound site 202 from instillation fluid reservoir 204 via supply tubing 208. In some embodiments, an entire volume of instillation fluid in instillation fluid reservoir 204 is provided to wound site 202. In some embodiments, pump 142 automatically provides a specific amount of instillation fluid from instillation fluid reservoir 204 to wound site 202. For example, in some embodiments instillation fluid reservoir 204 contains 500 mL of instillation fluid, but pump 142 operates to only provide 15 mL of instillation fluid to wound site 202. In some embodiments, pump 142 performs the fluid instillation cycle by providing the instillation fluid to wound site 202. In some embodiments, in response to providing X amount of instillation fluid to wound site 202 during the fluid instillation cycle, pump 142 transitions into a soak mode for a soak cycle, where the instillation fluid is allowed to soak into wound site 202. In some embodiments, the soak mode includes keeping pump 142 in an in-operational state for a predetermined amount of time to allow the instillation fluid to sufficiently soak into wound site 202. In some embodiments, in response to completing the fluid instillation cycle and the soak cycle (e.g., the soak cycle may be optional), pump 142 draws a negative pressure at $p_{sp}$ for a time period Δt via return tubing 210. In some embodiments, pump 142 draws the negative pressure at $p_{sp}$ to perform NPWT for a NPWT cycle. In some embodiments, over the course of NPWT, pump 142 transitions between fluid instillation cycles and NPWT cycles, thereby providing and removing instillation fluid to and from wound site 202.

Referring still to FIG. 2, wound site 202 includes a wound 218, a seal 214, and foam 216. In some embodiments, seal 214 is configured to seal along an entire perimeter of wound 218. In some embodiments, seal 214 is configured to seal along a periwound surface 212 surrounding wound 218. In some embodiments, seal 214 includes an adhesive to maintain and sealingly connect seal 214 to periwound surface 212. In some embodiments, seal 214 is configured to seal along a surface of a patient surrounding periwound surface 212. In some embodiments, seal 214 covers and seals substantially an entire surface which includes wound 218 therewithin. In some embodiments, seal 214 defines inner volume 250. In some embodiments, inner volume 250 is defined as any volume between seal 214 and a surface which seal 214 covers. For example, inner volume 250 may include an inner wound volume 222.

Supply tube 208 and return tube 210 are configured to sealingly connect to seal 214 such that they are fluidly coupled with inner volume 250. In some embodiments, return tube 210 provides a negative pressure produced by pump 142 to inner volume 250. In some embodiments, return tube 210 facilitates the egress of air, gas, or liquid within inner volume 250. Likewise, supply tube 208 is configured to provide instillation fluid to inner volume 250, according to some embodiments. In some embodiments, supply tube 208 is fluidly and sealingly connected with inner volume 250. In some embodiments, supply tube 208 and return tube 210 are sealingly and fluidly coupled to inner volume 250 defined by seal 214 via connectors 224 and 226, respectively.

Referring still to FIG. 2, foam 216 is shown disposed within inner volume 222 of wound 218, according to some embodiments. In some embodiments, foam 216 includes one or more pieces of foam configured to substantially fill inner volume 222 of wound 218. In some embodiments, foam 216 is configured to absorb instillation fluid provided from instillation fluid reservoir 204 via supply tube 208. In some embodiments, foam 216 is configured to prevent particulate matter (e.g., scar tissue, scabbing, etc.) from entering return tube 210. In some embodiments, foam 216 is GRANUFOAM™. Foam 216 includes exterior surface 234, according to some embodiments. In some embodiments, at least a portion of exterior surface 234 of foam 216 is substantially adjacent wound surface 220 of wound 218. In some embodiments, an entire portion of exterior surface 234 of foam 216 is adjacent wound surface 220 of wound 218. In some embodiments, foam 216 facilitates providing instillation fluid to wound 218 (e.g., at wound surface 220). In some embodiments, exterior surface 234 of foam 216 is in contact with wound surface 220 of wound 218.

Foam 216 includes edge 235, according to some embodiments. In some embodiments, edge 235 is or defines a perimeter of foam 216. Likewise, wound 218 includes edge 221, according to some embodiments. In some embodiments, edge 221 of wound is or defines a perimeter of wound 218. In some embodiments, wound 218 has a depth 232. In some embodiments, a perimeter of wound 218 increases with depth 232. For example, a perimeter of wound 218 may be greater than perimeter of wound 218 at periwound surface 212 (e.g., wound 218 may increase in overall size at various depths).

Wound and Foam Volume Changes

Referring now to FIGS. 3-6, wound 218 and foam 216 are shown in greater detail, according to some embodiments. As shown in FIG. 3, wound 218 has an overall width (or length), shown as distance 230 and foam 216 has an overall width (or length), shown as distance 228, according to some embodiments. In some embodiments, distance 228 of foam 216 is substantially equal to distance 230 of wound 218. In some embodiments, distance 228 of foam 216 is substantially equal to distance 230 of wound 218 at a beginning of NPWT. For example, foam 216 may be packed within inner volume 222 of wound 218 such that foam 216 fills substantially the entire inner volume 222 of wound 218. In some embodiments, foam 216 is compressible so that it can be packed into inner volume 222 of wound 218. In some embodiments, since foam 216 is compressible, it can change in shape, diameter, perimeter, length, area, volume, etc., throughout the course of NPWT.

In some embodiments, a required amount of instillation fluid $V_{instillation}$ changes throughout a course of NPWT. For example, in some embodiments, inner volume 222 of wound 218 changes (e.g., decreases) due to swelling (i.e., edema) of surrounding tissue or wound tissue, healing (e.g., wound 218 shrinks as wound 218 heals), granulation formation within wound 218, and compression of foam 216. In some embodiments, any of the hereinabove mentioned volume changes (e.g., granulation formation, healing, edema, compression, etc.) change the required amount of instillation fluid V. For example, in some embodiments, the required amount of instillation fluid V decreases over the course of NPWT. Other systems may overfill inner volume 250 with instillation fluid, thereby increasing the likelihood of leaks, seal breakage, and deteriorating the quality of NPWT. Additionally, a seal leak may allow air to enter inner volume 250 which may deteriorate the healing process and reduce the efficiency of pump 142. Advantageously, controller 110 is configured to decrease an amount of instillation fluid provided to inner volume 250 for subsequently occurring fluid instillation cycles, described in greater detail below.

The compression of foam 216 is a significant contributor to changes in the required amount of instillation fluid $V_{instillation}$, according to some embodiments. In some embodiments, foam 216 undergoes a compression set. In some embodiments, the compression set of foam 216 is the most significant factor in changes to the required amount of instillation fluid $V_{instillation}$ over time. In some embodiments, the compression of foam 216 is predictable based on any of an amount of compression (e.g., a negative pressure at inner volume 250, $p_{sp}$), a temperature applied to foam 216 (e.g., temperature of wound 218, human body temperature, etc.), and time (e.g., therapy time). In some embodiments, as foam 216 decreases in volume, height, width, area, perimeter, etc. (e.g., as foam 216 compresses), a fluid capacity ($C_{foam}$) of foam 216 decreases. In some embodiments, as foam 216 compression sets (e.g., fluid capacity $C_{foam}$ decreases), the required amount of instillation fluid $V_{instillation}$ decreases.

In some embodiments, when seal 214 is removed (e.g., during a dressing change, during a seal change, etc.), foam 216 is exposed to atmospheric pressure and expands. In some embodiments, the foam 216 increases back to an original height, width, volume, etc., in response to being exposed to atmospheric pressure. However, in some embodiments, foam 216 fails to expand back (e.g., re-inflate) to the original height, width, volume, etc. In some embodiments, foam 216 fails to expand back to the original height, width, volume, etc., as NPWT continues. For example, in some embodiments, foam 216 does not re-inflate to the original height due to instillation fluid or air present in foam 216 which was provided to foam 216 throughout the course of a previous NPWT implementation (e.g., a previous round of NPWT). Additionally, foam 216 may accumulate tissue matter which may reduce the fluid capacity of foam 216. In some embodiments, as NPWT continues, the amount by which foam 216 re-inflates (e.g., how close foam 216 returns to the original size, volume, height, width, etc.), decreases. In some embodiments, if foam 216 fails to re-inflate, this affects the static volume which foam 216 takes before foam 216 appears to inflate due to fluid being delivered. In some embodiments, controller 110 is configured adjust the required amount of instillation fluid $V_{instillation}$ provided to wound site 202 by NPWT application system 200 to account for an amount by which foam 216 compresses.

Referring now to FIGS. 3 and 4, foam 216 is shown before and after compressing, according to some embodiments. FIG. 3 may represent foam 216 before foam 216 receives instillation fluid. FIG. 4 represents foam 216 after foam 216 has been exposed to negative pressure and temperatures (e.g., human body temperature) for an amount of time, according to some embodiments. As shown in FIGS. 3-4, foam 216 has height 238 and wound 218 has height/depth 232. In some embodiments, height 238 of foam 216 is initially substantially equal to height/depth 232 of wound 218. In some embodiments, after foam 216 has been exposed to negative pressure and temperature (FIG. 4), for an amount of time (e.g., a therapy time), height 238 of foam decreases. As shown in FIG. 4, height 238 of foam 216 is less than height/depth 232 of wound 218 after foam 216 has been exposed to negative pressure and temperature for the amount of time, according to some embodiments. In some embodiments, the decrease in height 238 of foam 216 affects the required amount of instillation fluid $V_{instillation}$ to be provided to wound site 202.

Referring now to FIGS. 3-6, width 228 of foam 216 may decrease similar to the decrease in height 238 of foam 216, according to some embodiments. In FIGS. 3 and 5, foam 216 has an overall width 228 substantially equal to an overall width 230 of wound 218, according to some embodiments. In some embodiments, FIGS. 3 and 5 illustrate foam 216 before foam 216 has been exposed to negative pressure and a temperature for an amount of time. In some embodiments, as shown in FIG. 5, an overall perimeter 235 of foam 216 is initially substantially equal to perimeter 221 of wound 218. In some embodiments, after foam 216 has been exposed to negative pressure and temperature for some amount of time, overall perimeter 235 of foam 216 decreases as shown in FIG. 6. In some embodiments, the decrease in perimeter 235 of foam 216 is due to a decrease in width 228 of foam 216. As shown in FIG. 6, perimeter 235 of foam 216 has decreased an amount such that perimeter 235 is offset a distance 236 from perimeter 221 of wound 218. In some embodiments, the decrease in height 238 and/or width 228 and/or perimeter 235 of foam 216 affects the required amount of instillation fluid $V_{instillation}$ which should be provided to wound site 202. In some embodiments, the decrease in height 238, perimeter 221, and/or width 228 is related to the fluid capacity $C_{foam}$ of foam 216. For example, height 238 may decrease as well as perimeter 221, due to buildup of wound tissue matter within foam 216 which decreases the fluid capacity $C_{foam}$ of foam 216. In some embodiments, the fluid capacity $C_{foam}$ changing indicates a required change in the required amount of instillation fluid $V_{instillation}$ for wound 218.

Referring now to FIGS. 7-10, changes in overall size of wound 218 are shown, according to some embodiments. In some embodiments, wound 218 may change in overall size due to any of swelling, edema, and healing. In some embodiments, changes in overall size of wound 218 decreases inner volume 222 of wound 218. In some embodiments, as inner volume 222 of wound 218 change (e.g., decreases), the required amount of instillation fluid $V_{instillation}$ which should be provided to wound site 202 changes (e.g., decreases). In some embodiments, inner volume 222 of wound 218 decreases due to granulation formation.

Figure 7:
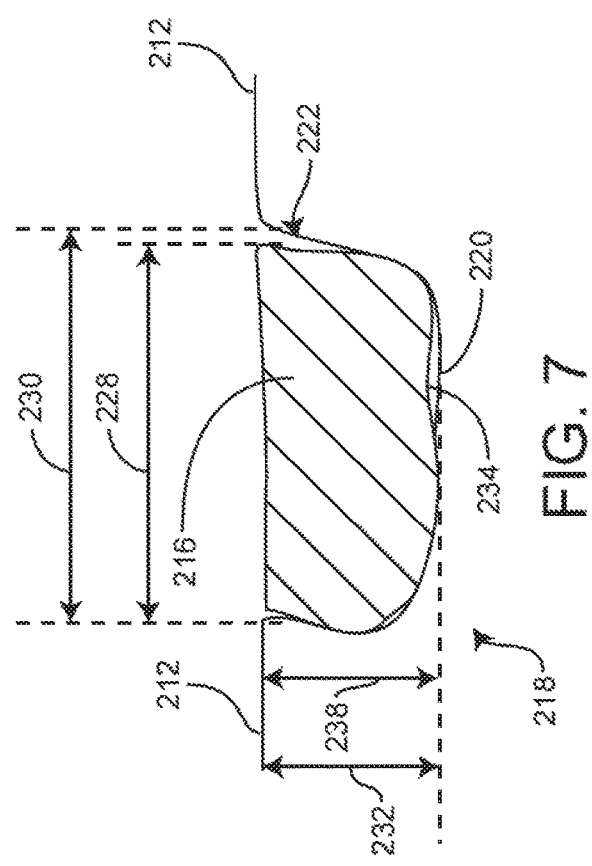
FIG. 7 is a side view of the dressing and the wound of the wound site of FIG. 2, according to some embodiments.
Figure 8:
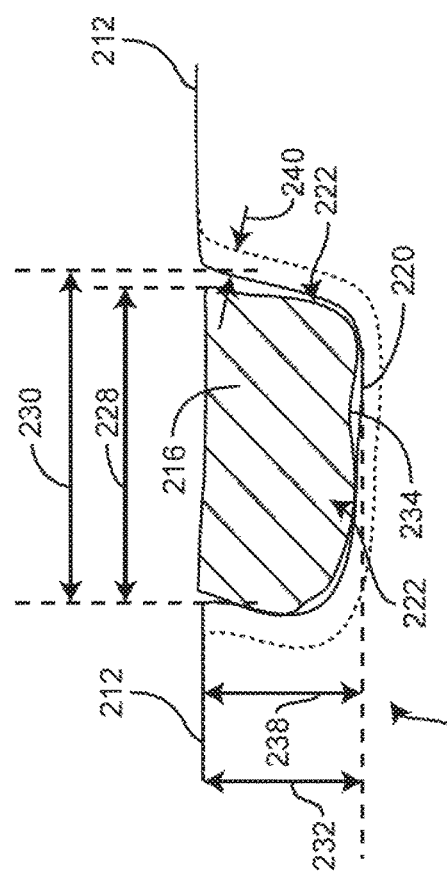
FIG. 8 is a side view of the dressing and the wound of the wound site of FIG. 2, after the wound has decreased in volume, according to some embodiments.

Referring now to FIG. 7, wound 218 is shown at an initial state, according to some embodiments. In some embodiments, the initial state of wound 218 as shown in FIG. 7 is a state of wound 218 before NPWT has begun. Wound 218 has an overall width 230 at the initial state, according to some embodiments. In some embodiments, wound 218 has an overall height 232 at the initial state. As shown in FIG. 8, as NPWT is performed on wound 218, at least one of overall width 230 and overall height 232 of wound decreases, according to some embodiments. In some embodiments, the decrease in either overall height 232 and overall width 230 of wound 218 decreases inner volume 222 of wound 218. In some embodiments, a decrease in inner volume 222 of wound 218 decreases the required amount of instillation fluid $V_{instillation}$ which should be provided to wound site 202 via supply tube 208. In some embodiments, controller 110 is configured to predict and offset the required amount of instillation fluid $V_{instillation}$ with respect to time to account for decreases in volume 222 of wound 218 as wound 218 heals. Inner volume 222 of wound 218 may decrease or change for any of the reasons listed herein above (e.g., healing, granulation tissue formation, swelling, edema, etc.), according to some embodiments.

Figure 9:
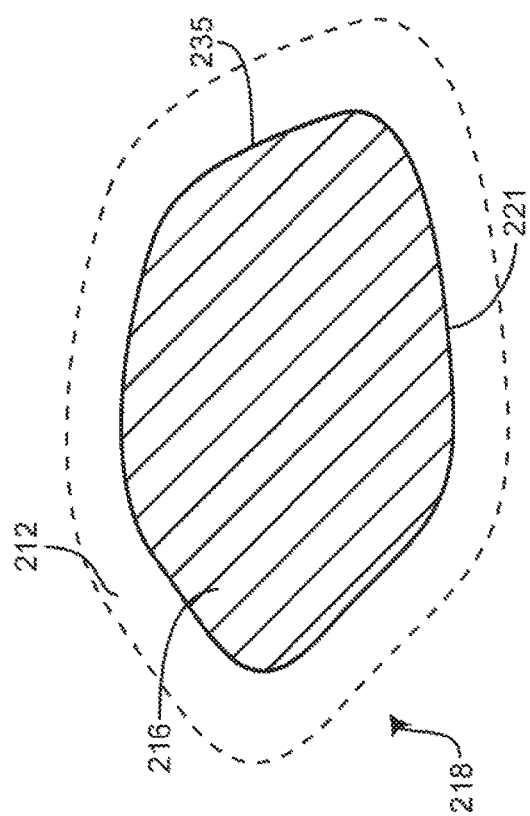
FIG. 9 is a top view of the dressing and the wound of the wound site of FIG. 2, according to some embodiments.
Figure 10:
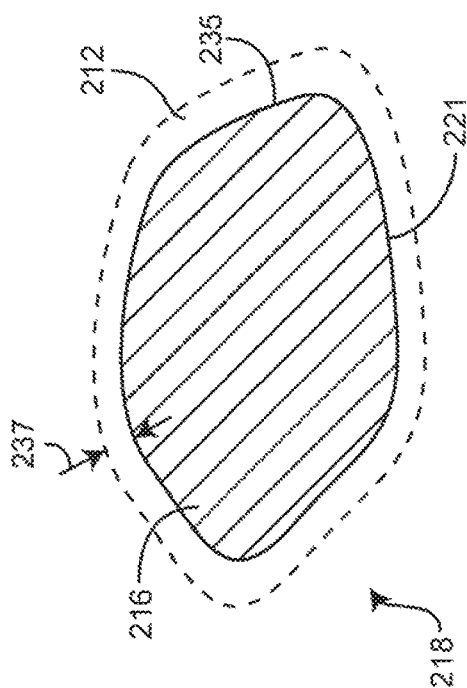
FIG. 10 is a top view of the dressing and the wound of the wound site of FIG. 2, after the wound has decreased in volume, according to some embodiments.

As shown in FIGS. 9-10, perimeter 221 of wound 218 may change as NPWT continues (e.g., due to edema, healing of wound 218, granulation tissue formation, swelling, etc.), according to some embodiments. In some embodiments, perimeter 221 of wound 218 decreases as NPWT continues due to any of the hereinabove mentioned factors. In some embodiments, as perimeter 221 of wound 218 decreases, the required amount of instillation fluid $V_{instillation}$ of wound 218 decreases. In some embodiments, foam 216 changes (e.g., decreases) in size, shape, perimeter, width, height, etc., as wound 218 changes. For example, as shown in FIG. 10, perimeter 221 of wound 218 has decreased an offset distance 237 relative to an initial perimeter 221 of wound 218, according to some embodiments. Likewise, perimeter 235 of foam 216 has also decreased, according to some embodiments.

Controller 110 is configured to adjust the required amount of instillation fluid $V_{instillation}$ provided to wound site 202 to account for any of volumetric changes of wound 218 and volumetric changes of foam 216, according to some embodiments. In some embodiments, controller 110 uses an empirical relationship to determine the required amount of instillation fluid $V_{instillation}$ and/or an amount to increase or decrease the required amount of instillation fluid $V_{instillation}$ to account for the changes in volume of wound 218 and/or the changes in volume of foam 216. In some embodiments, the changes in volume of foam 216 are due to compression setting of foam 216 as described above. In some embodiments, changes in volume of wound 218 are due to any of edema, swelling, wound healing, granulation tissue formation, etc.

Empirical Relationships

Figure 11:
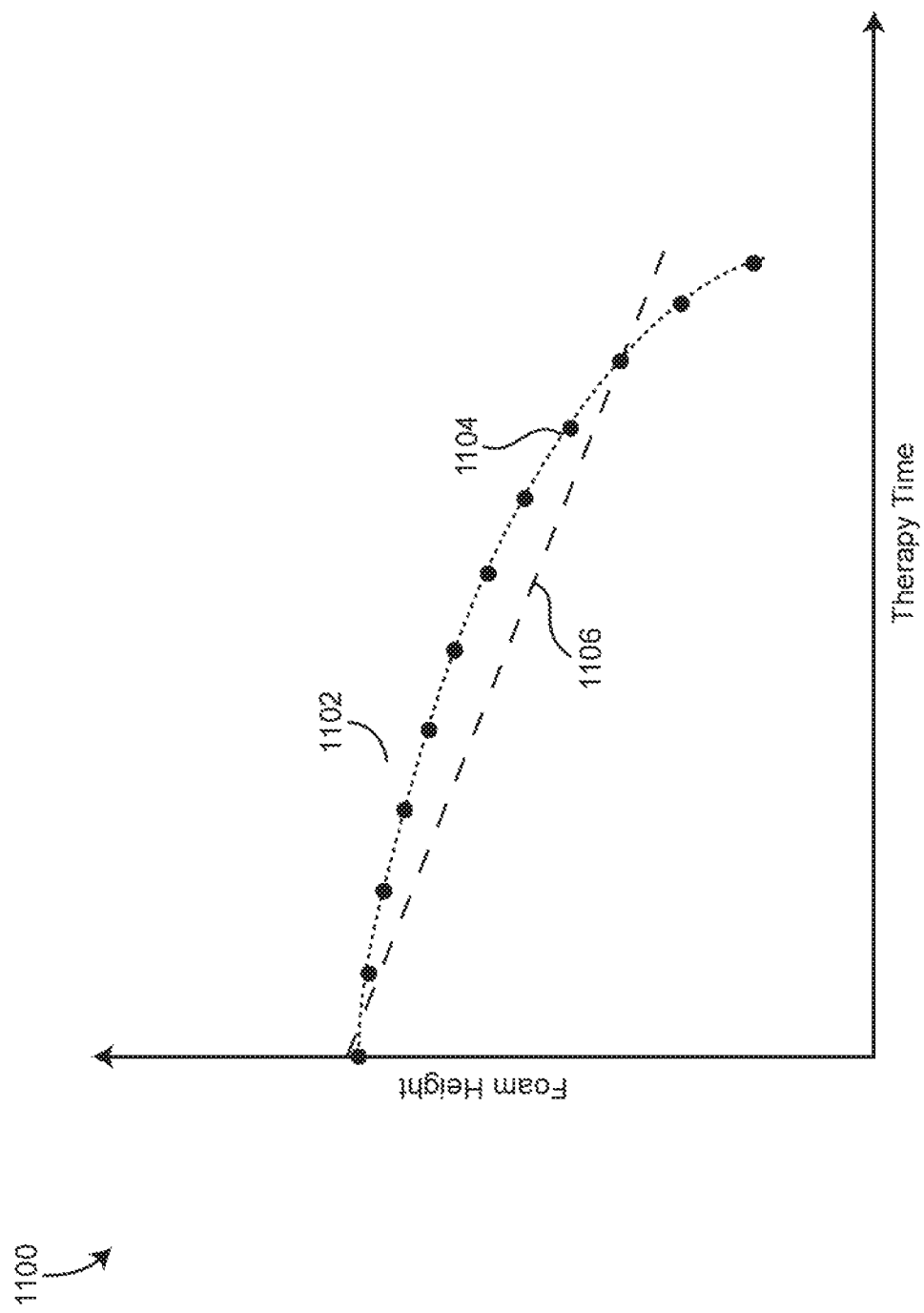
FIG. 11 is a graph of an empirical relationship between dressing/foam height and therapy time which may be used by the controller of FIG. 1 to determine an instillation fluid quantity, according to some embodiments.
Figure 12:
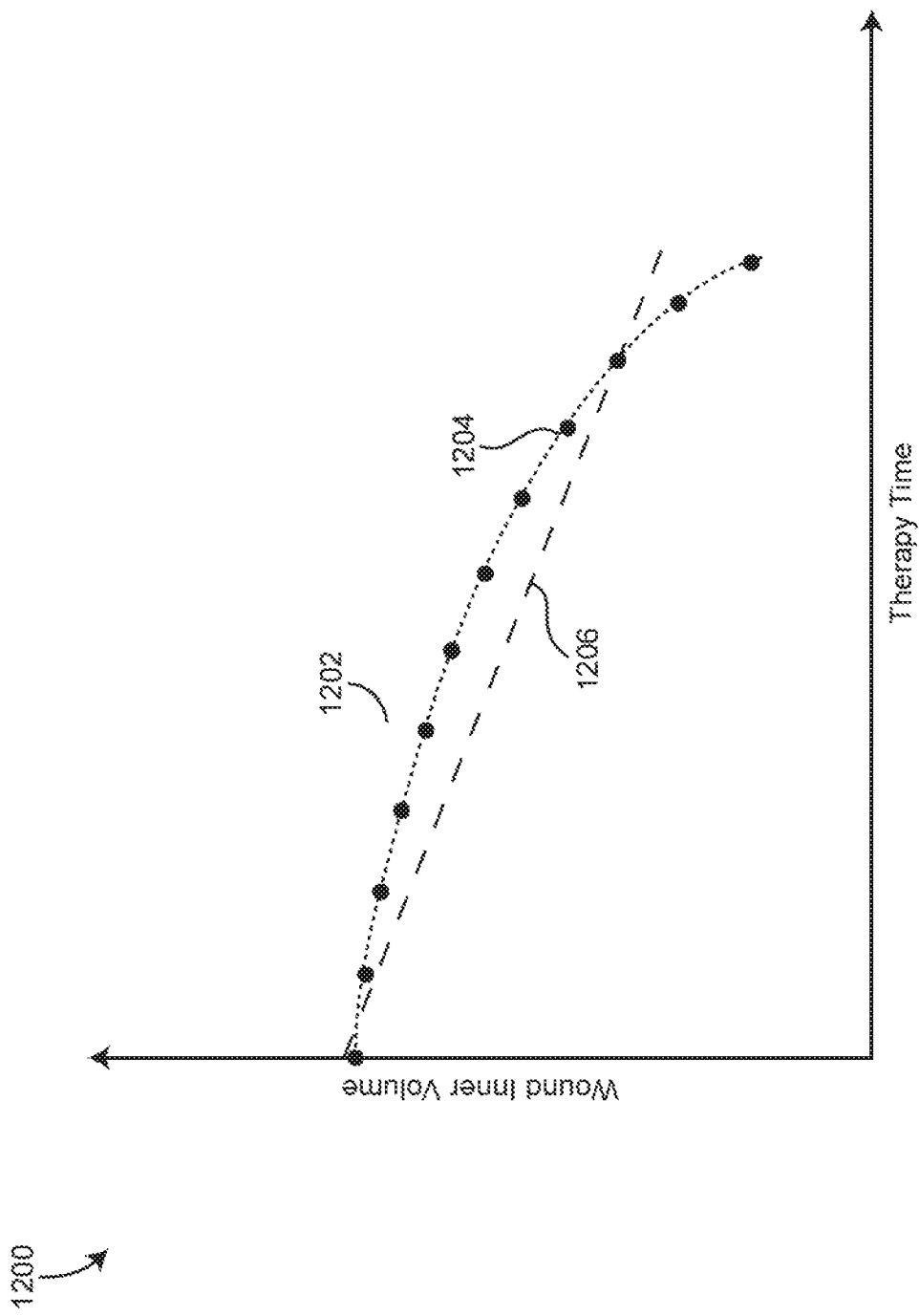
FIG. 12 is a graph of an empirical relationship between wound volume and therapy time, which may be used by the controller of FIG. 1 to determine an instillation fluid quantity, according to some embodiments.

Referring now to FIGS. 11-12, graphs 1100 and 1200 show changes in height of foam 216 and changes in volume of wound 218, according to some embodiments. In some embodiments, the empirical relationships shown in graphs 1100 and 1200 are used to determine factors which controller 110 uses to determine the required amount of instillation fluid $V_{instillation}$. In some embodiments, the empirical relationships shown in graphs 1100 and 1200 are used to determine an amount to increase or decrease the required amount of instillation fluid $V_{instillation}$. In some embodiments, a factor amount to increase or decrease the required amount of instillation fluid $V_{instillation}$ is referred to as the reduction factor θ.

Referring now to FIG. 11, graph 1100 shows the changes of height 238 of foam 216 (Y-axis) with respect to therapy time (X-axis), according to some embodiments. In some embodiments, graph 1100 includes scatter data 1102. In some embodiments, scatter data 1102 is empirical data determined through testing. In some embodiments, for example, scatter data 1102 is determined by measuring an initial value of height 238 of foam 216, performing NPWT for some amount of time, and measuring the value of height 238 of foam 216 after NPWT has been performed. For example, a single piece of foam 216 with an initial height 238 value of 30 mm may be exposed to a Saline solution (e.g., instillation fluid) at a negative pressure of 125 mmHg (e.g., $p_{sp}$) and at a temperature of 35 degrees Celsius (approximately human body temperature) for a predetermined amount of time (e.g., 24 hours), according to some embodiments. After the predetermined amount of time has elapsed, another value of height 238 of foam 216 is recorded (e.g., the value of height 238 of foam 216 is 29 mm), according to some embodiments. This process may be repeated to determine data points which relate height 238 of foam 216 to therapy time (e.g., to determine data point 1102) for a particular set of temperature and pressure ($p_{sp}$) conditions. For example, in some embodiments, after the foam with the initial value of height 238 of 30 mm was exposed to the same conditions for another 12 hours, the final value of height 238 was recorded at 28 mm, according to some embodiments. This yields the datapoints: h=30 mm at t=0 hours, h=29 mm at t=24 hours, and h=28 mm at t=36 hours for foam 216 when tested at 125 mmHg and 35 degrees Celsius, where h is height 238 of foam 216, according to some embodiments. This test may be continued to determine additional data points for various combinations of temperature and pressure, according to some embodiments. For example, this test may be performed for a negative pressure, $p_{sp}$, of 75 mmHg, 152 mmHg, 200 mmHg, etc., or any other $p_{sp}$ value which is typically used during NPWT, according to some embodiments.

Referring still to FIG. 11, a linear trendline 1106 or a non-linear relationship 1104 can be determined based on scatter data 1102 as determined using the testing procedure above, according to some embodiments. In some embodiments, a linear trendline 1106 and/or a non-linear relationship 1104 can be determined for each set of scatter data resulting from various test parameters (e.g., various values of $p_{sp}$, various temperature values, etc. In some embodiments, the relationship between change in height h (i.e., height 238 of foam 216) and therapy time has the relationship:

$$\Delta h = f_{foam}(T, \Delta t, p_{sp})$$

where $f_{foam}$ is a relationship between Δh and T, Δt, and $p_{sp}$, T is a temperature which the foam is exposed to during testing, Δt is an elapsed amount of therapy time, and $p_{sp}$ is a pressure to which the foam is exposed during testing. In some embodiments, $f_{foam}$ depends on various properties of the foam. In some embodiments, $f_{foam}$ is a linear relationship between Δt and Δh. In some embodiments, $f_{foam}$ is a non-linear relationship between Δt and Δh. In some embodiments, $f_{foam}$ is determined for each combination of T and $p_{sp}$ which may be used during NPWT. In some embodiments, multiple tests are performed for various sets of T and $p_{sp}$ and a multi-variable regression is performed to determine $f_{foam}$ for Δh in terms of T, Δt, and $p_{sp}$.

In some embodiments, the change in height Δh of foam 216 due to NPWT is proportional to fluid capacity of foam 216 (i.e., $C_{foam} \propto \Delta h$). In some embodiments, as the height h of foam 216 decreases, the fluid capacity $C_{foam}$ also decreases. In some embodiments, as the fluid capacity $C_{foam}$ decreases (e.g., due to compression set, tissue matter within foam 216, etc.), the required amount of instillation fluid $V_{instillation}$ also decreases. In this way, as foam 216 changes over time during NPWT, the required amount of instillation fluid $V_{instillation}$ also changes over time, according to some embodiments. Controller 110 is configured to decrease the amount of instillation fluid $V_{instillation}$ for subsequently occurring fluid instillation cycles based on Δt and $p_{sp}$, according to some embodiments.

Referring now to FIG. 12, graph 1200 shows the changes of inner volume 222 ($V_{wound}$) of wound 218 (Y-axis) with respect to therapy time (X-axis), according to some embodiments. In some embodiments, inner volume 222 of wound 218 is directly correlated to a fluid capacity of wound 218 (e.g., an amount of instillation fluid which wound 218 can contain). In some embodiments, graph 1200 includes scatter data 1202. In some embodiments, scatter data 1202 is a result of various tests. For example, scatter data 1202 may represent values of inner volume 222 of wound 218 as measured throughout a NPWT application, according to some embodiments. In some embodiments, scatter data 1202 is collected for various NPWT applications with various temperature T (e.g., various human body temperatures) and various negative pressure setpoints $p_{sp}$. In some embodiments, a linear trendline 1206 is fit to scatter data 1202 to determine a relationship between inner volume 222 of wound 218 and therapy time. In some embodiments, a non-linear relationship 1204 is determined based on scatter data 1202 to determine a non-linear relationship between inner volume 222 of wound 218 and therapy time. In some embodiments, trendline 1206 and/or non-linear relationship 1204 are used to predict an amount by which inner volume 222 of wound 218 decreases as NPWT is performed. Advantageously, controller 110 can use the predicted change in inner volume 222 of wound 218 to determine changes to the required amount of instillation fluid $V_{instillation}$.

In some embodiments, any of the relationships described herein above with reference to graphs 1100 and 1200 are used to determine the factor(s) θ which controller 110 uses to adjust the required amount of instillation fluid $V_{instillation}$. In some embodiments, controller 110 stores one or more values of θ for various NPWT parameters (e.g., various $p_{sp}$ values, various T values, combinations of the various $p_{sp}$ and T values, etc.) and uses the one or more values of θ to determine adjusted amounts of instillation fluid $V_{instillation}$. In some embodiments, controller 110 uses a function to determine the factor θ based on various NPWT parameters. In some embodiments the values of the factor θ are determined based on any of the relationships as shown in graphs 1100 and 1200.

Controller Configuration

Figure 13:
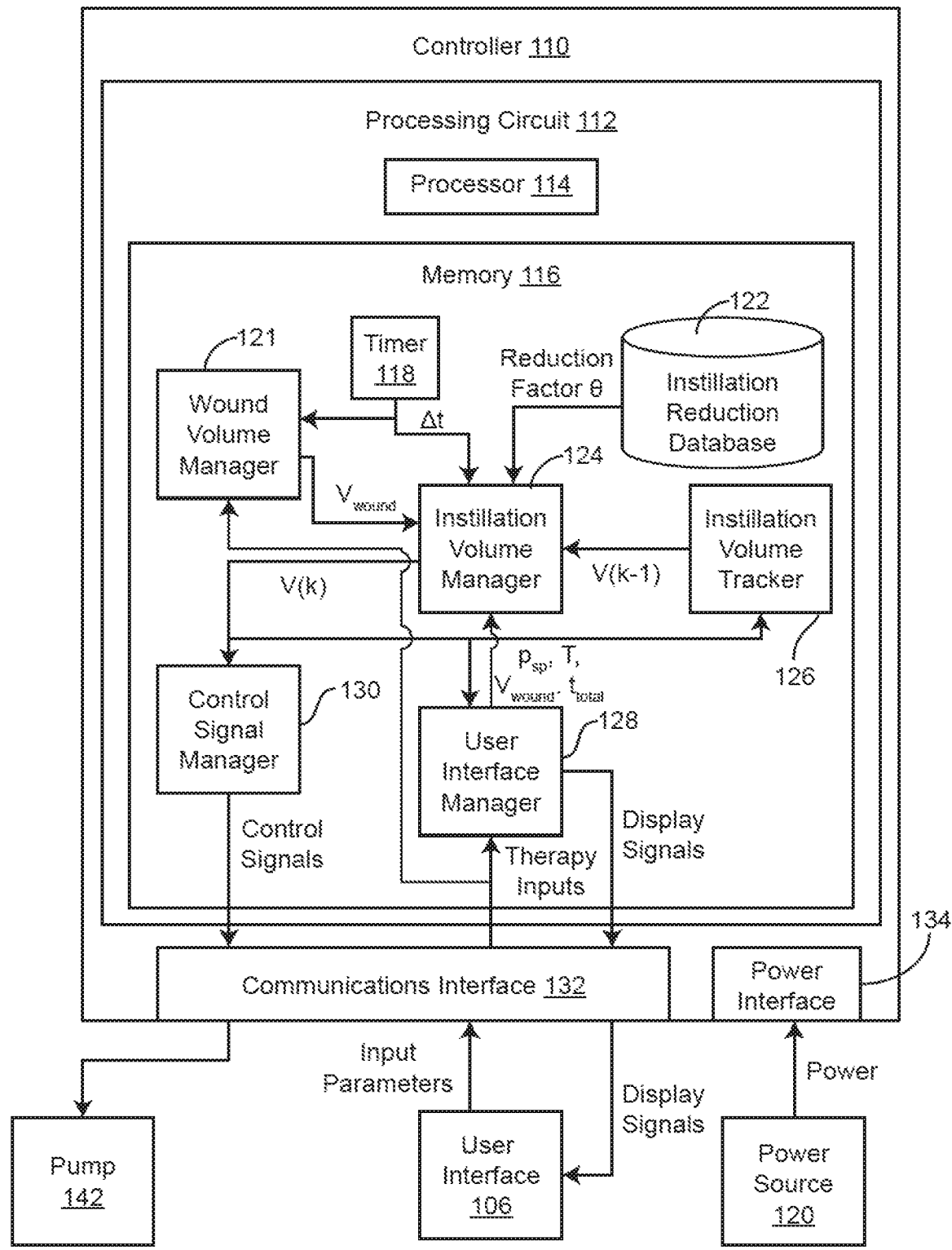
FIG. 13 is a block diagram of the controller of the NPWT device of FIG. 1, including an instillation volume manager retrieving a reduction factor from an instillation reduction database, according to some embodiments.

Referring now to FIG. 13, controller 110 is shown in greater detail, according to some embodiments. Controller 110 is configured to determine changes in the required amount of instillation fluid $V_{instillation}$ to ensure that an excess of instillation fluid is not provided to wound site 202, according to some embodiments. In some embodiments, controller 110 advantageously reduces the likelihood that an excessive amount of instillation fluid (e.g., saline solution) is introduced to wound site 202. Some systems may require a user to manually determine an amount of instillation fluid to be added to wound site 202. Advantageously, controller 110 is configured to automatically adjust the amount of instillation fluid introduced to wound site 202 to prevent leakages from occurring and to improve quality of the NPWT, according to some embodiments.

Controller 110 is configured to control an operation of pump 142 to perform the NWPT, according to some embodiments. In some embodiments, controller 110 is configured to control pump 142 and/or NPWT application system 200 to provide the determined instillation volume $V_{instillation}$ to wound site 202 for a fluid instillation cycle. Controller 110 is shown to include a processing circuit, shown as processing circuit 112, according to some embodiments. Processing circuit 112 may be configured to perform some or all of the functionality of controller 110. Processing circuit 112 is shown to include a processor, shown as processor 114. Processor 114 may be a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Processor 114 may be a microprocessor, or, any conventional processor, controller, microcontroller, or state machine. Processor 114 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. Processing circuit 112 also include memory, shown as memory 116. Memory 116 (e.g., memory, memory unit, storage device) may include one or more devices (e.g., RAM, ROM, Flash memory, hard disk storage) for storing data and/or computer code for completing or facilitating the various processes, layers and modules described in the present disclosure. Memory 116 may be or include volatile memory or non-volatile memory, and may include database components, object code components, script components, or any other type of information structure for supporting the various activities and information structures described herein. According to an exemplary embodiment, the memory 116 is communicably connected to the processor 114 via processing circuit 112 and includes computer code for executing (e.g., by the processing circuit or the processor) the one or more processes described herein.

Referring still to FIG. 13, controller 110 is shown to include a power interface, shown as power interface 134, according to an exemplary embodiment. Power interface 134 is configured to draw power supplied by a power source, shown as power source 120, to power controller 110, according to some embodiments. In some embodiments, power source 120 is any kind of permanent and/or temporary power source. In some embodiments, power source 120 is a battery. In some embodiments, power interface 134 is a connection port for a permanent power source (e.g., AC power and/or DC power) such as a wired 24 VAC connection. In other embodiments, power interface 134 includes both a port for permanent power and/or a power circuit configured to receive and transform power from power source 120. In some embodiments, power interface 134 is configured to receive power from both a permanent power source (e.g., an outlet) and a temporary power source (e.g., a battery). Power interface 134 may include any number of electrical components such as resistors, transistors, capacitors, inductors, diodes, transformers, transistors, switches, etc., necessary to receive, transform, and supply power to controller 110, according to some embodiments. In some embodiments, if power interface 134 is configured to receive power from a temporary power source (e.g., if power source 120 is a battery), power interface 134 may output power level data of power source 120 to processing circuit 112. The power level data may indicate an amount of energy remaining in power source 120 (e.g., a number of kW-hrs remaining in power source 120). In some embodiments, power source 120 is a replaceable power source (e.g., a battery). In some embodiments, power source 120 is one or more disposable batteries. For example, power source 120 is one or more disposable 12-volt batteries, according to some embodiments. In some embodiments, power source 120 is one or more rechargeable batteries. In some embodiments, power source 120 is configured to be temporarily disconnected from power interface 134 when the replaceable power source must be replaced (e.g., if power source 120 is one or more replaceable batteries, power source 120 may be disconnected when the battery level is low and the batteries must be replaced).

Referring still to FIG. 13, controller 110 is shown to include communications interface 132, according to some embodiments. Communications interface 132 is configured to facilitate communication between controller 110 and various external devices, sensors, systems, etc. Communications interface 132 is configured to receive inputs from at least one of pump 142, user interface 106, a sensor, a device, etc. according to some embodiments. In some embodiments, communications interface 132 receives commands and/or requests from user interface 106. For example, user interface manager 128 may receive a command from user interface 106 via communications interface 132 to transition NPWT device 100 between various modes of operation, or to adjust an operational characteristic of the NPWT being performed by NPWT device 100 (e.g., increasing a pressure setpoint, increasing an amount of therapy time, pausing therapy, etc.). Communications interface 132 is also configured to receive information from pump 142 regarding an actual therapy pressure or a pump duty, according to some embodiments. In some embodiments, communications interface 132 is configured to facilitate communications between user interface 106 and user interface manager 128. Communications interface 132 may include any wired or wireless interfaces. For example, communications interface 132 may include a Universal Serial Bus interface, according to some embodiments. In other embodiments, communications interface 132 includes one or more wireless transceivers configured to wirelessly communicably connect controller 110 with various external devices, systems, sensors, etc. (e.g., user interface 106 and pump 142). In some embodiments, communications interface 132 is configured to facilitate communications between control signal manager 130 and pump 142. For example, control signal manager 130 may determine control signals for pump 142 and/or NPWT application system 200. In some embodiments, communications interface 132 facilitates communications between pump 142 and control signal manager 130 such that control signal manager 130 can output control signals to pump 142 to adjust an operation of pump 142.

Referring still to FIG. 13, memory 116 is shown to include user interface manager 128, according to some embodiments. In some embodiments, user interface manager 128 is configured to receive one or more inputs from user interface 106. In some embodiments, user interface manager 128 is configured to receive one or more therapy parameters from user interface 106 via communications interface 132. The one or more therapy parameters may include any of a type of therapy selected, a therapy pressure setpoint $p_{sp}$, a temperature (e.g., a local temperature at wound site 202), a total therapy time $t_{total}$, and a volume of wound 218 $V_{wound}$. In some embodiments, user interface manager 128 receives a therapy selection from user interface 106 via communications interface 132 and determines one or more of $p_{sp}$, T, $t_{total}$, $V_{wound}$, etc. In some embodiments, user interface manager 128 provides any of $p_{sp}$, T, $V_{wound}$, and $t_{total}$ to instillation volume manager 124. In some embodiments, instillation volume manager 124 uses any of these inputs to determine an instillation fluid quantity (i.e., volume) $V_{instillation}$ using any of $p_{sp}$, T, $V_{wound}$, and $t_{total}$. In some embodiments, T is assumed to be normal body temperature of a human. In some embodiments, $p_{sp}$ is a negative pressure setpoint input by a user via user interface 106. In some embodiments, $p_{sp}$ is a negative pressure setpoint as determined by user interface manager 128 based on the type of therapy selected or received from user interface 106.

Referring still to FIG. 13, memory 116 is shown to include timer 118, according to some embodiments. In some embodiments, timer 118 is configured to track an elapsed amount of time for which NPWT has been performed. For example, timer 118 may record a start time, and compare the start time of NPWT to a present time value to determine a total amount of time over which NPWT has been performed, according to some embodiments. In some embodiments, timer 118 is configured to provide instillation volume manager 124 and/or wound volume manager 136 with the total amount of elapsed time. In some embodiments, the elapsed time is $\Delta t$. In some embodiments, timer 118 keeps track of times at which therapy is paused (e.g., for dressing changes). In some embodiments, timer 118 receives $p_{sp}$ from any of user interface manager 128, communications interface 132, etc. In some embodiments, if $p_{sp}$ changes (e.g., is increased from 75 mmHg to 100 mmHg), timer 118 records a time at which $p_{sp}$ was changed. In some embodiments, timer 118 tracks an amount of time for which NPWT has been provided at a specific therapy pressure $p_{sp}$. For example, if NPWT device 100 provides NPWT at 100 mmHg for a first time period, and 125 mmHg for a second time period, timer 118 tracks the amount of time of the first time period and the second time period, according to some embodiments. In some embodiments, timer 118 is configured to provide instillation volume manager 124 with an elapsed amount of time $\Delta t$ since the previous pressure setpoint $p_{sp}$ change. In some embodiments, timer 118 is configured to identify events (e.g., therapy start time, pressure setpoint $p_{sp}$ changes, etc.), and record an amount of time between sequentially occurring events $\Delta t$ and/or an amount of time elapsed since a previously occurring event $\Delta t$. Timer 118 may provide instillation volume manager 124 and/or wound volume manager 136 with $\Delta t$.

Referring still to FIG. 13, memory 116 is shown to include wound volume manager 136, according to some embodiments. In some embodiments, wound volume manager 136 is configured to determine a volume of wound 218 $V_{wound}$. In some embodiments, wound volume manager 136 is configured to provide instillation volume manager 124 with the determined volume of wound 218, $V_{wound}$. In some embodiments, wound volume manager 136 determines $V_{wound}$ based on any of an elapsed time since an initiation of NPWT $\Delta t$, an amount of elapsed time $\Delta t$ since a therapy pressure setpoint change $p_{sp}$, an initial wound volume $V_{wound,initial}$, and an empirical relationship. In some embodiments, $V_{wound,initial}$ is provided to wound volume manager 136 via user interface 106 and communications interface 132 at a beginning of NPWT. For example, a user may measure an initial volume of wound 218 and input the initial volume of wound 218 via user interface 106. In some embodiments, wound volume manager 136 uses the empirical relationship described in greater detail above with reference to FIG. 12 to determine a current volume of wound 218. For example, wound volume manager 136 may receive an elapsed time since an initiation of NPWT, a pressure at which NPWT is being performed $p_{sp}$, and use the empirical relationship to determine a present value of $V_{wound}$. In some embodiments, wound volume manager 136 determines an amount by which $V_{wound}$ has decreased over a time period (e.g., since an initiation of NPWT). In some embodiments, wound volume manager 136 provides instillation volume manager 124 with $V_{wound}$.

Referring still to FIG. 13, memory 116 is shown to include instillation volume tracker 126, according to some embodiments. In some embodiments, instillation volume tracker 126 is configured to record/track instillation volumes $V_{instillation}$ over previous cycles of NPWT. For example, instillation volume tracker 126 may record the amount of instillation fluid $V_{instillation}$ provided to wound site 202 during a previous fluid instillation cycle (e.g., at fluid instillation cycle k−1), according to some embodiments. In some embodiments, instillation volume tracker 126 records and tracks an amount of instillation fluid (e.g., $V_{instillation}$) provided to wound 218 over a previous fluid instillation cycle. In some embodiments, instillation volume tracker 126 receives an instillation volume amount $V_{instillation}(k)$ as determined by instillation volume manager 124 for a current fluid instillation cycle (e.g., a current cycle of NPWT, a current fluid instillation cycle, etc.). For example, if NPWT device 100 is currently set to instill $X_1$ cubic centimeters of instillation fluid over an instillation fluid cycle and then provide NPWT at $p_{sp}=100$ mmHg for a 24 hour NPWT cycle, instillation volume tracker 126 records the $X_1$ cubic centimeters of instilled fluid for the first fluid instillation cycle. If NPWT device 100 is set to next instill $X_2$ cubic centimeters of instillation fluid over a second instillation fluid cycle and then provide NPWT at $p_{sp}=125$ mmHg for a second 24 hour NPWT cycle, instillation volume tracker 126 can provide the $X_1$ cubic centimeters to instillation volume manager 124 as the previously instilled quantity of instillation fluid $V_{instillation}(k-1)$ which can be used by instillation volume manager 124 to determine $X_2$ for the second instillation fluid cycle. When the second 24 hour NPWT cycle is completed, instillation volume tracker 126 may store $X_2$ as the previously instilled quantity of instillation fluid $V_{instillation}(k-1)$ and may store the instillation quantity $X_1$ from the first cycle as $V_{instillation}(k-2)$. In this way, instillation volume tracker 126 records instillation quantity for previously completed NPWT or fluid instillation cycles, according to some embodiments. In some embodiments, instillation volume tracker 126 also records and provides instillation volume manager 124 with a time duration $\Delta t$ of a previously performed NPWT cycle, and a NPWT pressure setpoint $p_{sp}(k-1)$ of the previously performed NPWT cycle.

Referring still to FIG. 13, memory 116 is shown to include instillation volume manager 124, according to some embodiments. In some embodiments, instillation volume manager 124 is configured to determine an amount of instillation fluid $V_{instillation}$ which should be provided to wound site 202. In some embodiments, instillation volume manager 124 is configured to determine $V_{instillation}$ based on any of an amount of elapsed therapy time (e.g., $\Delta t$), a therapy pressure setpoint $p_{sp}$, a type of NPWT being performed, and reduction factor θ. In some embodiments, instillation volume manager 124 receives the reduction factor θ from instillation reduction database 122. In some embodiments, instillation reduction database 122 includes a look-up table of various values for θ for different combinations of T and $p_{sp}$. In some embodiments, the various values of θ as stored in instillation reduction database 122 and provided to instillation volume manager 124 are determined using empirical test results, as described in greater detail above.

In some embodiments, instillation volume manager 124 determines a quantity (e.g., volume, amount, etc.) of instillation fluid $V_{instillation}(k)$ to be provided to wound 218 for a present instillation cycle k. In some embodiments, for a first fluid instillation cycle, instillation volume manager 124 determines that the first quantity of instillation fluid is $V_{wound}$ as determined by wound volume manager 121 or received from user interface manager 128. In some embodiments, for subsequently occurring fluid instillation cycles, instillation volume manager 124 determines the quantity of instillation fluid $V_{instillation}(k)$ to be provided to wound 218 for the present instillation cycle k based on the instillation fluid provided to wound 218 for the previous fluid instillation cycle. In some embodiments, instillation volume manager 124 determines the quantity of instillation fluid $V_{instillation}(k)$ to be provided to wound 218 for the present instillation cycle k using the equation:

$$V_{instillation}(k) = V_{instillation}(k-1) - \theta \cdot V_{instillation}(k-1)$$

where $V_{instillation}(k)$ is an amount of instillation fluid (e.g., in cubic centimeters) to be provided to wound 218 for a current fluid instillation cycle k, θ is a reduction factor, and $V_{instillation}(k-1)$ is an amount of instillation fluid (e.g., in cubic centimeters, in mL, etc.) which was provided to wound 218 for a previous fluid instillation cycle k−1, according to some embodiments. In some embodiments, the term $\theta \cdot V_{instillation}(k-1)$ is an amount by which to decrease the value of the previously provided instillation fluid quantity $V_{instillation}(k-1)$. In some embodiments, the reduction factor θ is a normalized value (e.g., between 0 and 1). In some embodiments, the reduction factor θ is a percentage value. In some embodiments, the reduction factor θ is selected by instillation volume manager 124 from instillation reduction database 122. In some embodiments, the reduction factor θ is selected or determined based on a previous NPWT cycle. In some embodiments, the reduction factor θ is selected or determined based on both a NPWT pressure setpoint $p_{sp}$ of a previous NPWT cycle, and an amount of time Δt for which the NPWT at $p_{sp}$ was provided to wound 218. In some embodiments, the reduction factor θ is determined using a function:

$$\theta = f_{reduc}(\Delta t, p_{sp})$$

where θ is the reduction factor, $p_{sp}$ is the NPWT pressure setpoint of the previous negative pressure cycle, Δt is a time duration over which NPWT was performed at $p_{sp}$ for the previous NPWT cycle, and $f_{reduc}$ is a relationship between θ and $p_{sp}$ and Δt. In some embodiments, $f_{reduc}$ is a function determined based on empirical data. In some embodiments, $f_{reduc}$ is determined based on an estimated amount of change in $V_{wound}$ over the time period Δt at the NPWT pressure setpoint $p_{sp}$ (e.g., due to edema, swelling, changes in foam 216, healing, etc.).

Figure 14:
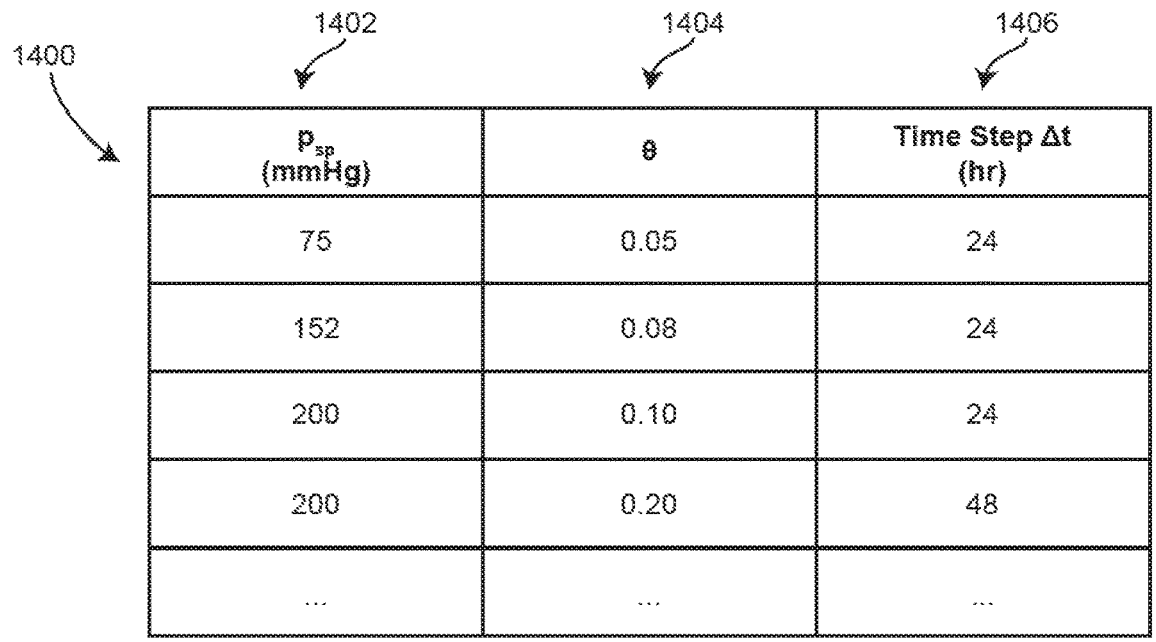
FIG. 14 is a table of reduction factors of the instillation reduction database of FIG. 13, according to some embodiments.

In some embodiments, the reduction factor θ is selected from a table of values stored in instillation reduction database 122. For example, instillation reduction database 122 may include table 1400 as shown in FIG. 14. Table 1400 includes a column 1402 which represents the pressure setpoint $p_{sp}$ of the previously provided NPWT, as well as a column 1406 of the time duration Δt over which the NPWT was provided at $p_{sp}$. Table 1400 includes column 1404 with values of the reduction factor θ, according to some embodiments. In some embodiments, instillation volume manager 124 retrieves an appropriate value of the reduction factor θ from table 1400 as stored in instillation reduction database 122 based on $p_{sp}$ and Δt. For example, as shown in FIG. 14, if NPWT was previously provided to wound 218 at a vacuum pressure of $p_{sp}$=75 mmHg for Δt=24 hours, the reduction factor θ is 0.05 (or a 5% reduction, according to some embodiments. In some embodiments, instillation volume manager 124 receives the previously provided quantity/volume of instillation fluid $V_{instillation}(k-1)$ from instillation volume tracker 126. For example, if at a previous fluid instillation cycle 30 cm³ of instillation fluid was provided to wound 218, and the reduction factor θ is 0.05 (e.g., for $p_{sp}$=75 and Δt=24 hrs), instillation volume manager 124 determines the volume of instillation fluid for a current fluid instillation cycle:

$$V_{instillation}(k) = 30 \text{ cm}^3 - 0.05 \cdot 30 \text{ cm}^3 = 30 \text{ cm}^3 - 1.5 \text{ cm}^3 = 28.5 \text{ cm}^3$$

according to some embodiments.

In some embodiments, instillation volume manager 124 receives an estimated/approximated current volume of wound 218 from wound volume manager 121. In some embodiments, instillation volume manager 124 receives the estimated/approximated current volume of wound 218 from user interface manager 128. In some embodiments, instillation volume manager 124 uses the estimated current volume of wound 218 to determine the reduction factor θ. In some embodiments, instillation volume manager 124 determines the reduction factor θ based on the wound volume $V_{wound}$ using the function:

$$\theta = f_{reduc, V_{wound}}(V_{wound}(k), V_{wound}(k-1))$$

where $V_{wound}(k)$ is the estimated volume of wound 218 received from wound volume manager 121 or user interface 106 at a present fluid instillation cycle k, $V_{wound}(k-1)$ is a previously estimated volume of wound 218 at a prior fluid instillation cycle, and $f_{reduc, V_{wound}}$ is a function which relates θ to $V_{wound}(k)$ and $V_{wound}(k-1)$.

Figure 16:
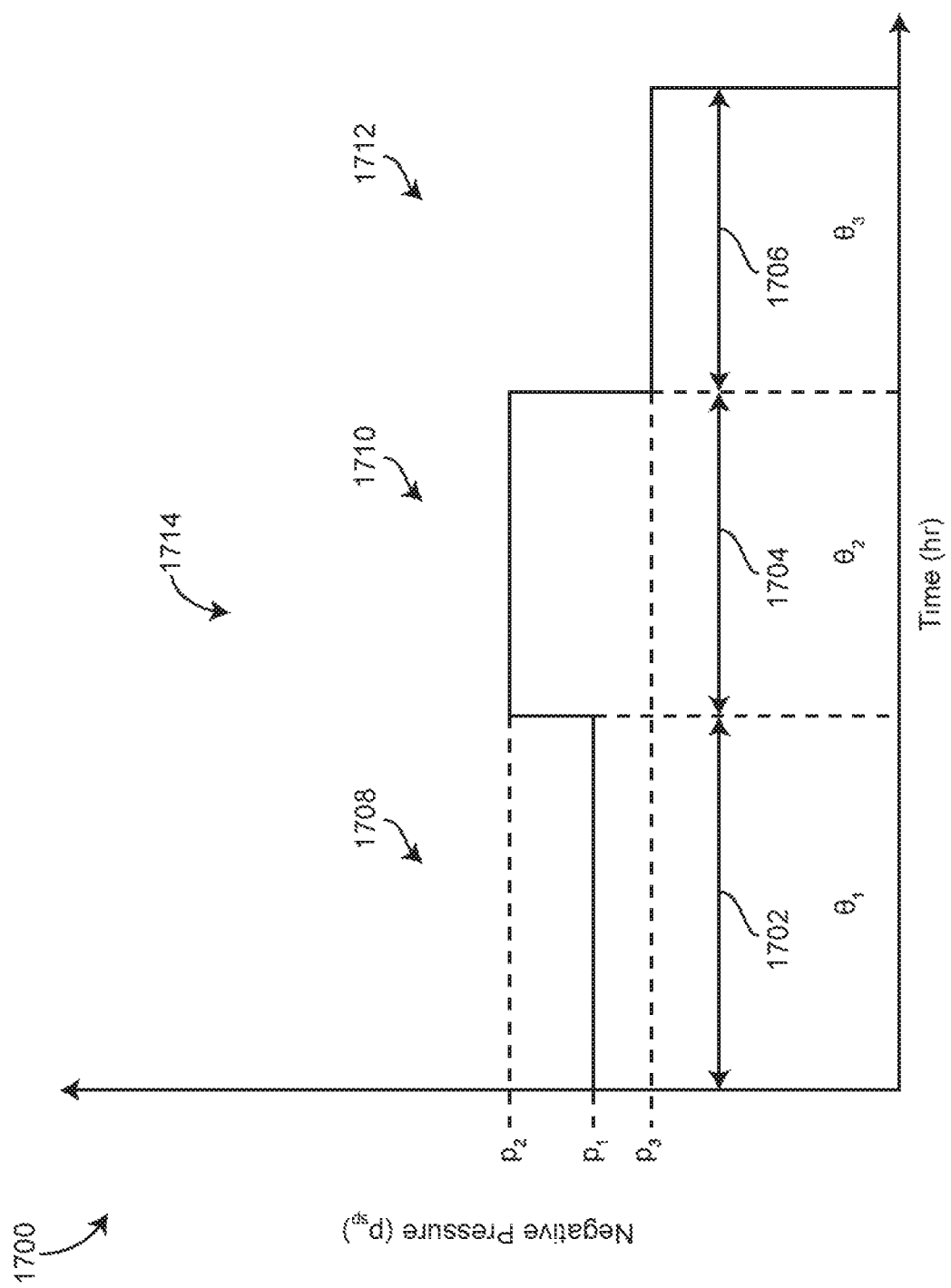
FIG. 16 is a graph of a NPWT cycle having multiple sections defined by a change in therapy pressure, according to some embodiments.

In some embodiments, a NPWT cycle may include changes in $p_{sp}$ at various points in the NPWT cycle. Graph 1700 of FIG. 16 illustrates a NPWT cycle 1714 having multiple stages, according to some embodiments. Graph 1700 illustrates provided negative pressure $p_{sp}$ (Y-axis) with respect to elapsed time (X-axis), according to some embodiments. In some embodiments, NPWT cycle 1714 includes a first portion 1708, a second portion 1710, and a third portion 1712. First portion 1708 has a time duration 1702 (i.e., $\Delta t_1$) at $p_{sp}=p_1$, second portion 1710 has a time duration 1704 (i.e., $\Delta t_2$) at $p_{sp}=p_2$, and third portion 1712 has a time duration 1706 (i.e., $\Delta t_3$) at $p_{sp}=p_3$, according to some embodiments. In some embodiments, $p_{sp}$ increases from first portion 1708 to second portion 1710, and decreases from second portion 1710 to third portion 1712. In some embodiments, instillation volume manager 124 treats each of portions 1708-1712 as individual portions and determines $V_{instillation}$ for a fluid instillation cycle following NPWT cycle 1714 by determining a reduction factor θ for each portion. In some embodiments, time durations 1702-1706 are recorded by timer 118. In some embodiments, instillation volume manager 124 uses the equation:

$$V_{instillation}(k) = V_{instillation}(k-1) - \sum_{i=1}^{n} V_{instillation}(k-1) \cdot \theta_i$$

where n is a number of portions/sections of a NPWT cycle which occurred between instillation cycle k and instillation cycle k−1 (e.g., 3 for the example as shown in FIG. 16), and $\theta_i$ is the reduction factor for each of the portions/sections of the NPWT cycle (e.g., NPWT cycle 1714).

For NPWT cycle 1714, the above equation reduces to:

$$V_{instillation}(k) = V_{instillation}(k-1) - V_{instillation}(k-1)(\theta_1 + \theta_2 + \theta_3)$$

where $\theta_1 = f_{reduc}(\Delta t_1, p_1)$, $\theta_2 = f_{reduc}(\Delta t_2, p_2)$, and $\theta_3 = f_{reduc}(\Delta t_3, p_3)$. Each of the reduction factors $\theta_1$, $\theta_2$, and $\theta_3$ may be determined using a function $f_{reduc}$ or by selecting an appropriate reduction factor from instillation reduction database 122 based on $\Delta t$ and $p_{sp}$. The above equation reduces to:

$$V_{instillation}(k) = V_{instillation}(k-1)\left(1 - \sum_{i=1}^{n} \theta_i\right)$$

according to some embodiments. In some embodiments, n indicates a number of portions of a NPWT cycle between the fluid instillation cycle k and the fluid instillation cycle k−1. In some embodiments, n is determined based on a number of changes of the NPWT pressure $p_{sp}$ as identified by timer 118. In some embodiments, installation volume manager 124 determines a number of portions of a NPWT cycle as:

$$n = \#p_{sp} \text{ changes} + 1$$

where $\#p_{sp}$ changes is a number of changes of $p_{sp}$ over the entire NPWT cycle. If, however, the NPWT cycle is performed at a single pressure (e.g., $p_{sp}$=150 mmHg), $\#p_{sp}$ changes is zero, and n is one. In some embodiments, the number of portions of the NPWT cycle indicates a number of reduction factors $\theta$.

In some embodiments, for a NPWT cycle (e.g., NPWT cycle 1714) having multiple sections, instillation volume manager 124 treats each section/portion as an individual NPWT cycle. For example, instillation volume manager 124 may determine a reduction factor $\theta$ for each portion/section, and determine an adjusted volume of instillation fluid $V_{instillation}$ for each section/portion. However, the "previous" instillation fluid volume $V_{instillation}(k-1)$ for subsequently occurring portions/sections is set equal to the instillation fluid $V_{instillation}$ for the immediately prior occurring portion/section, according to some embodiments. For example, for NPWT cycle 1714, section 1708 has reduction factor $\theta_1$, section 1710 has reduction factor $\theta_1$, and section 1712 has reduction factor $\theta_3$, according to some embodiments. In some embodiments, instillation volume manager 124 uses the equation:

$$V_{instillation}(k) = V_{instillation}(k-1) \prod_{i=1}^{n}(1 - \theta_i)$$

where n is a number of sections of the NPWT cycle due to pressure setpoint changes, $V_{instillation}(k-1)$ is an instillation fluid volume provided to the wound during a fluid instillation cycle prior to the NPWT cycle, and $V_{instillation}(k)$ is the amount of instillation fluid to be provided to the wound at a fluid instillation cycle following the NPWT cycle, according to some embodiments.

For example, if $\Delta t_1$ is 24 hours and $p_1$ is 152 mmHg, $\Delta t_2$ is 24 hours and $p_2$ is 200 mmHg, and $\Delta t_a$ is 24 hours and $p_3$ is 75 mmHg, $\theta_1$=0.08, $\theta_2$=0.10, and $\theta_3$=0.05 as determined by referencing table 1400, according to some embodiments. Assuming, for the sake of example, that the previously provided instillation volume $V_{instillation}(k-1)$ was 100 mL, the instillation volume to be provided for the fluid instillation cycle following NPWT cycle 1714 can be determined as:

$$V_{instillation}(k) = (V_{instillation}(k-1))(1 - \theta_1)(1 - \theta_2)(1 - \theta_3)$$
$$= 100 \text{ mL}(1 - 0.08)(1 - 0.10)(1 - 0.05)$$
$$= 100 \text{ mL}(0.7866)$$
$$= 78.66 \text{ mL}$$

according to some embodiments.

Alternatively, the instillation fluid volume $V_{instillation}(k)$ can be determined using the equation:

$$V_{instillation}(k) = V_{instillation}(k-1)\left(1 - \sum_{i=1}^{n} \theta_i\right)$$

which becomes:

$$V_{instillation}(k) = 100 \text{ mL}(1-(0.08+0.10+0.05)) = 100 \text{ mL}(0.77) = 77 \text{ mL}$$

according to some embodiments.

In some embodiments, for a NPWT cycle with multiple portions due to changes in the pressure setpoint $p_{sp}$, an average pressure across the entire NPWT cycle is determined. For example, for NPWT cycle 1714 as shown in FIG. 16, an average setpoint $p_{avg}$ can be determined as:

$$p_{avg} = \frac{(p_1 + p_2 + p_3)}{3}$$

which can be generalized as:

$$p_{avg} = \frac{\sum_{i=1}^{n} p_i}{n}$$

according to some embodiments.

In some embodiments, the instillation volume $V_{instillation}(k)$ for a fluid instillation cycle following NPWT cycle 1714 can then be determined using the equation:

$$V_{instillation}(k) = (V_{instillation}(k-1))(1-\theta_{avg})$$

where $\theta_{avg}$ is a reduction factor selected or determined based on an overall $\Delta t$ of NPWT cycle 1714 (e.g., $\Delta t_1 + \Delta t_2 + \Delta t_3$), and $p_{avg}$.

In some embodiments, $p_{avg}$ is a weighted average based on an amount of time for which each particular $p_{sp}$ was provided. For example, $p_{avg}$ may be determined using the equation:

$$p_{avg} = p_1\left(\frac{\Delta t_1}{\Delta t_1 + \Delta t_2 + \Delta t_3}\right) + p_2\left(\frac{\Delta t_2}{\Delta t_1 + \Delta t_2 + \Delta t_3}\right) + p_3\left(\frac{\Delta t_3}{\Delta t_1 + \Delta t_2 + \Delta t_3}\right)$$

or more generally:

$$p_{avg} = \sum_{i=1}^{n} p_i\left(\frac{\Delta t_i}{\Delta t_{total}}\right)$$

where $\Delta t_{total}$ is a total amount of time of the NPWT cycle, and n is a number of portions/sections of the NPWT cycle. This value of $p_{avg}$ may then be used by instillation volume manager 124 to determine or select the reduction factor θ.

In some embodiments, instillation volume manager 124 determines $V_{instillation}(k)$ for an upcoming fluid instillation cycle and provides $V_{instillation}(k)$ (also shown as V(k)) to control signal manager 130. In some embodiments, instillation volume manager 124 also provides the value of $V_{instillation}(k)$ to instillation volume tracker 126 for use in determining future values of $V_{instillation}(k)$. In some embodiments, control signal manager 130 receives the value of $V_{instillation}(k)$ and determines control signals for pump 142 to deliver/provide the value of $V_{instillation}(k)$ to wound 218 for a fluid instillation cycle. In some embodiments, control signal manager 130 adjusts an operation of pump 142 and/or an instillation/fluid delivery pump to provide $V_{instillation}(k)$ instillation fluid to wound site 202.

In some embodiments, instillation volume manager 124 provides user interface manager 128 with the value of $V_{instillation}(k)$. In some embodiments, user interface manager 128 determines display signals and provides the display signals to user interface 106. In some embodiments, user interface manager 128 adjusts an operation of user interface 106 such that user interface 106 displays the value of $V_{instillation}(k)$ to a user. In some embodiments, this facilitates providing the user with an indication of how much instillation fluid to put in instillation fluid reservoir 204. For example, in some embodiments, pump 142 is configured to deliver an entirety of instillation fluid present in instillation fluid reservoir 204 to wound site 202. If user interface manager 128 causes user interface 106 to display $V_{instillation}(k)$, the user knows how much instillation fluid to provide to instillation fluid reservoir 204 for pump 142 to provide to wound site 202.

In some embodiments, a user may replace foam 216 at dressing change stages. In some embodiments, user interface 106 is configured to receive a user input indicating that foam 216 has been replaced with fresh foam 216. In some embodiments, user interface 106 is configured to provide user interface manager 128 with an indication of the changed foam 216. In some embodiments, user interface manager 128 is configured to reset instillation volume manager 124 in response to a change of foam 216. In some embodiments, wound volume manager 121 re-calculates an initial wound volume $V_{wound}$ after foam 216 has been replaced. In some embodiments, user interface manager 128 causes user interface 106 to prompt a user to input wound volume $V_{wound}$ at user interface 106. In some embodiments, instillation volume manager 124 receives $V_{wound}$ from at least one of wound volume manager 121 and user interface manager 128 and determines an initial instillation volume $V_{instillation}(k)$. Replacing foam 216 causes instillation volume manager 124 to "reset" such that instillation volume reductions calculated since the previous dressing change are no longer relevant, according to some embodiments. However, instillation volume manager 124 may still account for volume changes due to wound healing (e.g., changes in $V_{wound}$), but since foam 216 has been replaced, the changes in instillation fluid volume due to foam compression and clogging (e.g., reduced $C_{foam}$) are no longer relevant. In some embodiments, instillation volume manager 124 essentially "re-starts" in response to foam 216 being replaced.

In some embodiments, instillation volume manager 124 accounts for a selected soak time of foam 216. For example, allowing foam 216 to soak for a period of time after the delivery of instillation fluid but before the application of negative pressure can reduce the effect of compression set of foam 216. In some embodiments, instillation volume manager 124 modifies (e.g., reduces) the reduction factor θ based on the soak time $\Delta t_{soak}$. In some embodiments, instillation volume manager 124 determines an adjusted reduction factor $\theta_{adj}$ which accounts for the soak time $\Delta t_{soak}$. In some embodiments, instillation volume manager 124 uses the equation:

$$\theta_{adj} = \theta - \Delta\theta_{soak}$$

where $\Delta\theta_{soak}$ is an adjustment amount determined based on $\Delta t_{soak}$ (e.g., $\Delta\theta_{soak} = f(\Delta t_{soak})$). In some embodiments, the longer foam 216 is allowed to soak, the greater $\Delta\theta_{soak}$ is, and therefore the adjusted reduction factor $\theta_{adj}$ is decreased. In some embodiments, the soak time $\Delta t_{soak}$ is defined as an amount of time after the instillation fluid has been provided to wound site 202 but before a negative pressure has been drawn at wound site 202. In some embodiments, the soak time $\Delta t_{soak}$ is input by a user via user interface 106.

Figure 17:
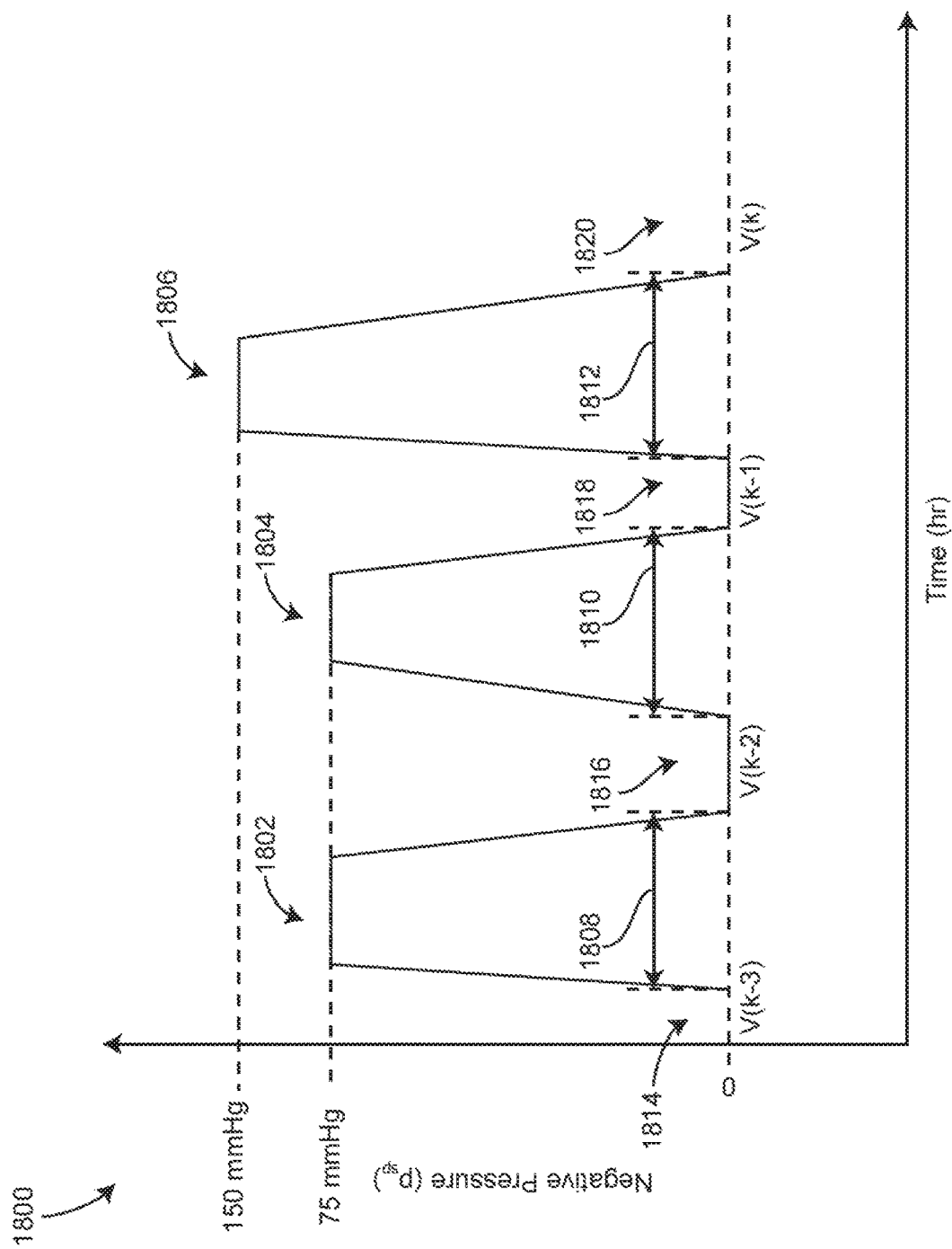
FIG. 17 is a graph of multiple NPWT cycles and instillation cycles over a time period, according to some embodiments.
Figure 18:
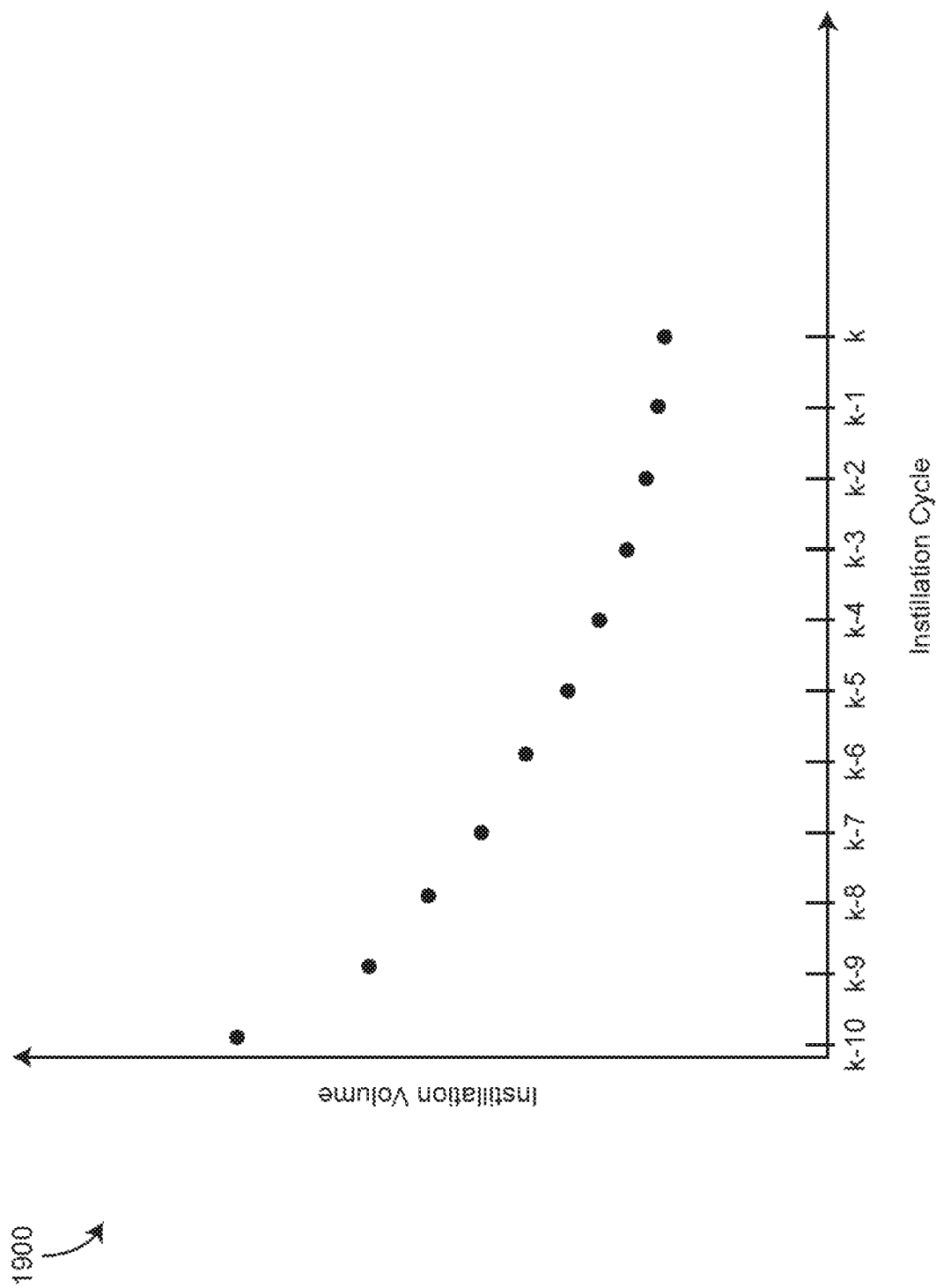
FIG. 18 is a graph of various instillation volume values for instillation cycles over a time period, according to some embodiments.

Referring now to FIG. 17, graph 1800 demonstrates the operation of controller 110 over time, according to some embodiments. Graph 1800 illustrates several NPWT cycles, shown as NPWT cycle 1802, NPWT cycle 1804, and NPWT cycle 1806, according to some embodiments. There are fluid instillation cycles before NPWT cycle, shown as instillation cycle 1814, instillation cycle 1816, and instillation cycle 1818, according to some embodiments. NPWT cycle 1802 is shown performed at 75 mmHg vacuum pressure for a time duration 1808, NPWT cycle 1804 is shown performed at 75 mmHg vacuum pressure for a time duration 1810, and NPWT cycle 1806 is shown performed at 150 mmHg vacuum pressure for a time duration 1812, according to some embodiments. In some embodiments, instillation fluid volume $V_{instillation}(k-3)$ was provided at instillation cycle 1814, $V_{instillation}(k-2)$ was provided at instillation cycle 1816, and $V_{instillation}(k-1)$ was provided at instillation cycle 1818. To determine $V_{instillation}(k)$ for a present instillation cycle 1820, controller 110 selects an appropriate reduction factor θ from instillation reduction database 122 based on the vacuum pressure (i.e., 150 mmHg) of the previously performed NPWT cycle (i.e., NPWT cycle 1806), and a time duration of the previously performed NPWT cycle (i.e., time duration 1812), according to some embodiments. Controller 110 then determines $V_{instillation}(k)$ using the equation:

$$V_{instillation}(k) = (V_{instillation}(k))(1-\theta)$$

according to some embodiments. After instillation cycle 1820 has been performed, $V_{instillation}(k)$ is then stored as $V_{instillation}(k-1)$ for future instillation cycles, according to some embodiments. Likewise, $V_{instillation}(k-1)$ for instillation cycle 1818 was determined based on NPWT cycle 1804 (i.e., time duration 1810, vacuum pressure 75 mmHg) and $V_{instillation}(k-2)$, $V_{instillation}(k-2)$ for instillation cycle 1816 was determined based on NPWT cycle 1802 (i.e., time duration 1808, vacuum pressure 75 mmHg), and $V_{instillation}$ (k−3), etc., according to some embodiments.

Referring now to FIG. 19, graph 1900 shows the change in instillation volume provided to a wound (e.g., wound 218) over time, according to some embodiments. The Y-axis of graph 1900 indicates a volume of instillation fluid provided to wound site 202 for a corresponding instillation cycle (the X-axis), according to some embodiments. As shown in graph 1900, since each volume of instillation fluid is determined based on a previous value of provided instillation fluid, the decrease over time is non-linear. In some embodiments, graph 1900 may be linear if controller 110 decreases the instillation volume for each instillation cycle by a standard amount.

Control Algorithm Method

Figure 15:
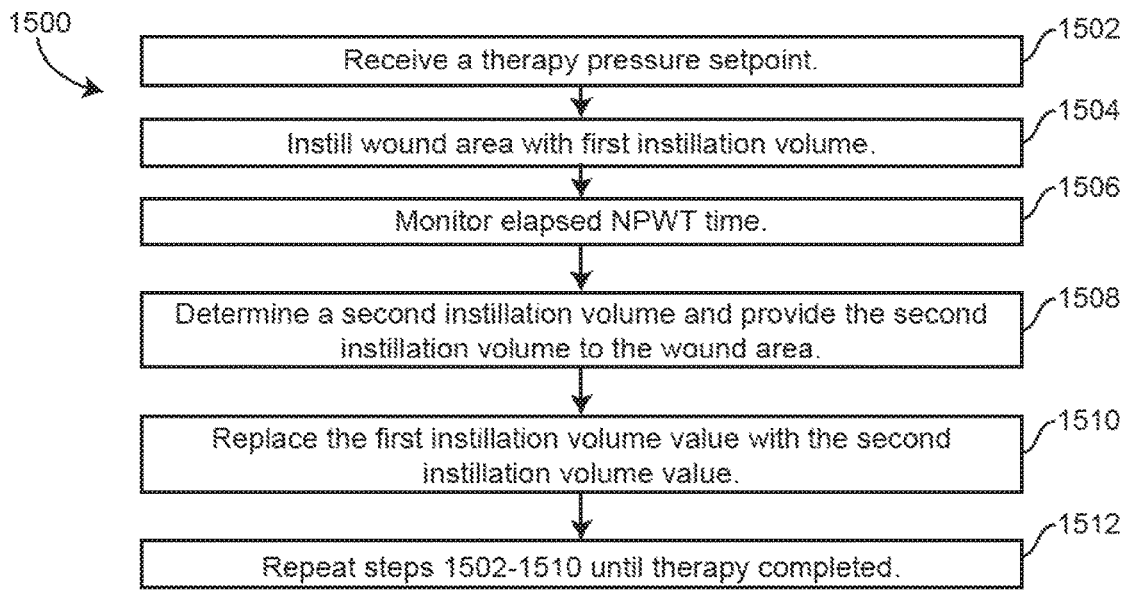
FIG. 15 is a method of determining adjusted instillation volumes for a NPWT device which may be used by the controller of the NPWT device of FIG. 1, according to some embodiments.

Referring now to FIG. 15, a process 1500 for determining an amount of instillation fluid to provide to a wound for NPWT is shown, according to some embodiments. In some embodiments, process 1500 is performed by controller 110. In some embodiments, process 1500 is performed by one or more components of controller 110 (e.g., by instillation volume manager 124).

Process 1500 includes receiving a therapy pressure setpoint $p_{sp}$ (step 1502), according to some embodiments. In some embodiments, the therapy pressure setpoint $p_{sp}$ is a vacuum pressure setpoint for a NPWT cycle. In some embodiments, the therapy pressure setpoint $p_{sp}$ is received by user interface manager 128. In some embodiments, the therapy pressure setpoint is received by instillation volume manager 124. In some embodiments, the therapy pressure setpoint is received by timer 118 for monitoring an amount of time NPWT is provided to the wound at the therapy pressure setpoint.

Process 1500 includes instilling a wound area with a first instillation volume (step 1504), according to some embodiments. In some embodiments, step 1504 includes determining an initial instillation volume as the first instillation volume. In some embodiments, the initial instillation volume is determined based on an estimated wound volume. In some embodiments, the estimated wound volume is provided to controller 110 via user interface 106. In some embodiments, the wound volume is estimated by wound volume manager 121. In some embodiments, instillation volume manager 124 is configured to receive the estimated wound volume to determine the initial instillation volume. In some embodiments, instillation volume manager 124 uses the wound volume and a relationship between wound volume and required instillation fluid to determine the initial instillation volume. In some embodiments, the relationship used by instillation volume manager 124 to determine the initial instillation volume is an empirical relationship. In some embodiments, control signal manager 130 receives the initial instillation volume from instillation volume manager 124 and adjusts an operation of pump 142 to provide wound site 202 with the initial volume of instillation fluid.

Process 1500 includes monitoring an amount of elapsed NPWT time (step 1506), according to some embodiments. In some embodiments, the amount of elapsed time is monitored by timer 118. In some embodiments, the amount of elapsed time is an amount of time for which NPWT has been performed at the therapy pressure setpoint as received in step 1502. In some embodiments, the monitored elapsed time is provided to instillation volume manager 124.

Process 1500 includes determining a second instillation volume and providing the second instillation volume of instillation fluid to the wound area (step 1508), according to some embodiments. In some embodiments, the new or adjusted instillation volume is decreased relative to the initial or first (i.e., previously provided) instillation volume. In some embodiments, the second instillation volume is determined based on a reduction factor θ. In some embodiments, the reduction factor θ is determined based on the therapy pressure setpoint, and the amount of elapsed time for which NPWT was provided at the therapy pressure setpoint. In some embodiments, step 1508 is performed by instillation volume manager 124. In some embodiments, step 1508 includes any of the functionality of instillation volume manager 124 to determine $V_{instillation}(k)$.

Process 1500 includes replacing the first instillation volume value with the second instillation volume value (step 1510), according to some embodiments. In some embodiments, the first instillation volume value is replaced by the second, most recently determined instillation volume value, in response to step 1508 being completed. In some embodiments, step 1510 is performed by instillation volume tracker 126.

Process 1500 includes repeating steps 1502-1510 until therapy is completed (step 1512), according to some embodiments. In some embodiments, step 1512 is performed by controller 110. In some embodiments, step 1502-1510 are repeated until NPWT is completed, or until a user changes dressings of the wound.

Configuration of Exemplary Embodiments

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A negative pressure wound therapy (NPWT) system comprising:
    an installation system configured to provide installation fluid to a wound site, wherein the wound site comprises a wound and a wound dressing;
    a controller configured to:
        provide a first quantity of installation fluid for a first installation cycle;
        determine a second quantity of installation fluid for a second installation cycle based on the first quantity and a reduction factor, wherein the second quantity of installation fluid is less than the first quantity of installation fluid; and
        adjust an operation of the installation system to provide the second quantity of installation fluid to the wound site,
    wherein the reduction factor is determined based on a negative pressure of a negative pressure cycle and a time duration of the negative pressure cycle.

2. The NPWT system of claim 1, wherein the wound dressing comprises one or more foam pieces.

3. The NPWT system of claim 1, wherein the controller is configured to receive an initial volume value of the wound from a user interface and use the initial volume value of the wound to determine the first quantity of installation fluid.

4. The NPWT system of claim 1, wherein the controller is configured to determine the second quantity of installation fluid for the second installation cycle by determining a decrease amount based on the reduction factor and the first quantity.

5. The NPWT system of claim 4, wherein the second quantity is a difference between the first quantity and a product of the first quantity and the reduction factor.

6. The NPWT system of claim 1, wherein the reduction factor is a normalized value.

7. The NPWT system of claim 1, wherein the controller is configured to select the reduction factor from a database of reduction factors based on the negative pressure of the negative pressure cycle and the duration of the negative pressure cycle.

8. A negative pressure wound therapy (NPWT) system comprising:
    an installation system configured to provide installation fluid to a wound site, wherein the wound site comprises a wound and a wound dressing;
    a controller configured to:
        provide a first quantity of installation fluid for a first installation cycle;
        determine a second quantity of installation fluid for a second installation cycle based on the first quantity and a reduction factor, wherein the second quantity of installation fluid is less than the first quantity of installation fluid; and
        adjust an operation of the installation system to provide the second quantity of installation fluid to the wound site,
    wherein the reduction factor is determined based on an amount of compression of the wound dressing over a time period.

9. The NPWT system of claim 8, wherein the wound dressing comprises one or more foam pieces.

10. The NPWT system of claim 8, wherein the controller is configured to receive an initial volume value of the wound from a user interface and use the initial volume value of the wound to determine the first quantity of installation fluid.

11. The NPWT system of claim 8, wherein the controller is configured to determine the second quantity of installation fluid for the second installation cycle by determining a decrease amount based on the reduction factor and the first quantity.

12. The NPWT system of claim 11, wherein the second quantity is a difference between the first quantity and a product of the first quantity and the reduction factor.

13. The NPWT system of claim 8, wherein the reduction factor is a normalized value.

* * * * *